(12) United States Patent
Ravikumar

(10) Patent No.: US 6,967,247 B2
(45) Date of Patent: Nov. 22, 2005

(54) DEPROTECTION OF PHOSPHORUS IN OLIGONUCLEOTIDE SYNTHESIS

(75) Inventor: Vasulinga Ravikumar, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 31 days.

(21) Appl. No.: 10/201,799

(22) Filed: Jul. 24, 2002

(65) Prior Publication Data

US 2004/0024194 A1 Feb. 5, 2004

(51) Int. Cl.$^7$ .......................... C07H 21/02; C07H 21/04
(52) U.S. Cl. .................................. 536/25.31; 536/25.3
(58) Field of Search .............................. 536/25.3, 25.31

(56) References Cited

U.S. PATENT DOCUMENTS

| | | | |
|---|---|---|---|
| 4,458,066 A | | 7/1984 | Caruthers et al. .............. 536/27 |
| 4,711,847 A | * | 12/1987 | Konig et al. ................ 435/68.1 |
| 4,725,677 A | | 2/1988 | Koster et al. ................. 536/27 |
| RE34,069 E | | 9/1992 | Koster et al. ................. 536/27 |

OTHER PUBLICATIONS

Copy of the PCT International Search Report dated Oct. 23, 2003 (PCT/US03/22211).

Kumar, R. et al., "The First Analogues of LNA (Locked Nucleic Acids): Phosphorothioate–LNA and 2'–THI-O–LNA," *Bioorganic & Medicinal Chem. Letts.*, 1998, 8, 2219–2222.

Singh, S. K. et al., "Synthesis of 2'–Amino–LNA: A Novel Conformationally Restricted High–Affinity Oligonucleotide Analogue with a Handle," *J.Org.Chem.*, 1998, 63, 10035–10039.

\* cited by examiner

*Primary Examiner*—James O. Wilson
*Assistant Examiner*—Patrick Lewis
(74) *Attorney, Agent, or Firm*—Isis Patent Department Woodcock Washburn LLP

(57) ABSTRACT

A process for removing a phosphorus protecting group from a protected phosphate triester or phosphorothioate triester includes contacting a protected phosphate or phosphorothioate triester with a thiol compound that is not offensive to the olfactory senses.

44 Claims, No Drawings

DEPROTECTION OF PHOSPHORUS IN OLIGONUCLEOTIDE SYNTHESIS

FIELD OF THE INVENTION

The present invention is directed to the field of organic synthetic chemistry. In particular, the present invention provides a method of selective deprotection of a protected phosphorus in oligonucleotide synthesis.

BACKGROUND OF THE INVENTION

It is well-known that most of the biological processes in animals, including pathological processes, are governed on the cellular level by proteins. Acting directly (e.g. structurally) or through their enzymatic functions, proteins contribute to many pathological processes in animals and humans. While classical therapeutic methods have generally focused on interactions between chemical compounds and proteins, some investigators haw recently focused on treating disease states by modulating the intracellular manufacture of proteins through interactions between putative therapeutic compounds and intracellular genetic material, such as polynucleotides. Such investigators have proven that modulating the production of proteins through interactions with intracellular polynucleotides, such as mRNA, can produce therapeutic results. Polynucleotide-focused drug discovery efforts have produced therapeutic compounds possessing excellent therapeutic activity and minimal undesirable side effects.

One method for specific modulation of gene expression is through the activity of oligonucleotides or oligonucleotide analogs as "antisense" agents. In general, "antisense" methodology involves specific and selective interaction between oligonucleotides or oligonucleotide analogs and complimentary intracellular nucleic acid sequences (e.g. single stranded DNA or mRNA) to modulate transcription or translation of the sequences. In many cases, the interaction between oligonucleotides or oligonucleotide analogs and their intracellular compliments takes place through complimentary base pairing, also known as Watson-Crick hybridization, although other modes of hybridization are also possible.

As oligonucleotides and oligonucleotide analogs have acquired acceptance as promising therapeutic agents, the demand for such compounds has greatly increased. Experimentation has provided three principal methods for the synthesis of oligonucleotides. Reese described the phosphotriester method in *Tetrahedron* 1978, 34, 3143; Beaucage described the phosphoramidite method in *Methods in Molecular Biology: Protocols for Oligonucleotides and Analogs*; Agrawal, ed., Humana Press: Totowa, 1993, Vol. 20, 33–61; and Froehler described the H-phosphonate method in *Methods in Molecular Biology: Protocols for Oligonucleotides and Analogs* Agrawal, ed.; Humana Press: Totowa, 1993, Vol. 20, 63–80. Of these three synthetic methods, the phosphoramidite method has become the preferred method for synthesizing oligonucleotides on a solid support. The phosphoramidite method includes a step of binding a first 5'-protected nucleoside via the 3'-O to a linker that is in turn conjugated to a solid support. The 5'-protecting group is then removed and a 5'-protected-3'-nucleoside phosphoramidite having a phosphorus protecting group is allowed to react with the support-bound nucleoside, whereby the amine function of the amidite is displaced by the 5'-O of the support-bound nucleoside. The phosphorus, which is in the P(III) oxidation state, can then be oxidized (e.g. sulfurized) to form the P(V) oxidation state. The deprotection, amidite reaction and oxidation steps are repeated until the desired chain length is completed. Once the desired oligonucleotide chain length has been achieved, the phosphorus protecting groups are removed, the oligonucleotide is cleaved from the solid support, and the ultimate 5'-protecting group is cleaved from the oligonucleotide.

In principle, a suitable phosphorus protecting group can be any group that is labile under selective conditions, but that will protect the phosphorus from attack during amidite chain-lengthening, phosphorus oxidation and 5'-deprotection. For instance, Caruthers et al. have taught phosphorus protection using a methyl group ($-CH_3$). See U.S. Pat. Nos. 4,458,066, 4,500,707, 5,132,418, 4,415,732, 4,668,777 and 4,973,679. Caruthers et al. taught removal of the $CH_3$ protecting group (phosphorus-deprotection) by thiophenol in the presence of triethylamine. This procedure for deprotection of methyl-protected phosphoramidites, however, suffers a few notable drawbacks.

One such drawback is that thiophenol is a foul smelling reagent, which is extremely difficult and unpleasant to use. Also, as salts of thiphenol can clog the tubing of automated synthesizers, the user must be careful to maintain reaction conditions within tightly controlled parameters. Thiophenol can also induce methylation of thymine, an undesirable side reaction that alters the structure and the properties of the final oligonucleotide product. Further, removal of methyl groups by this procedure requires reaction periods that can be as long as, or longer than, the time required to synthesize the oligonucleotides. These drawbacks in the removal of alkyl phosphorus-protecting groups have led to the development of alternative approaches to phosphorus-protection and deprotection.

Köster et al. have disclosed a different type of phosphorus protecting group, cyanoethyl, that has gained wide acceptance. See U.S. Pat. Nos. 4,725,677 and Re. 34,069. The cyanoethyl phosphorus protecting group is removed by β-elimination under weakly basic conditions, rather than by direct nucleophilic substitution. While the Köster methodology provides a facile approach to phosphorus deprotection, and is considered an improvement over the Caruthers methodology, it suffers from some drawbacks of its own. For one, cyanoethylphosphoramidites are relatively costly. Also, the free acrylonitrile moiety that arises from β-elimination of the cyanoethyl group can form undesirable adducts. Additionally, acrylonitrile itself is considered toxic, and it would be desirable to reduce, if not eliminate entirely, its production in processes for making pharmaceutical compounds.

There is thus a need for a phosphorus protection/deprotection scheme that would not suffer the drawbacks of using a malodorous deprotecting reagent, such as thiophenol.

There is also a need for a phosphorus protection/deprotection scheme that would provide faster deprotection than dealkylation with thiophenol and triethylamine.

There is also a need for a phosphorus deprotection scheme that would not suffer the drawback of using expensive cyanoethyl protecting groups in the starting materials.

There is also a need for a phosphorus protection/deprotection scheme that would not suffer the drawback of releasing acrylonitrile during deprotection.

There is also a need for such a phosphorus protection/deprotection scheme that can be conveniently carried out using existing automated oligonucleotide synthesizers.

There is thus a need for a method for synthesizing an oligonucleotide that would avoid the disadvantages of using the cyanoethyl group as a phosphorus protecting group during chain elongation.

There is further a need for a non-malodorous reagent capable of removing a phosphorus protecting group from a protected phosphorus during synthesis of oligonucleotides and oligonucleotide analogs.

There is further a need for a method of using a cost effective, non-malodorous reagent for removal of a phosphorus protecting group.

SUMMARY OF THE INVENTION

The foregoing and other needs are met by embodiments of the present invention, which provide a process for removing a phosphorus protecting group from a phosphate or thiophosphate triester, thereby producing a phosphate or thiophosphate diester, which process comprises contacting the phosphorus-protected phosphate or thiophosphate triester with a non-malodorous thiol deprotecting agent under conditions and for a time sufficient to remove the phosphorus protecting group.

The foregoing and other needs are met by embodiments of the present invention, which provide a method of using a phosphorus-deprotecting compound of the formula Ia or Ib:

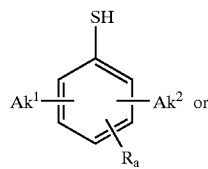

Ia

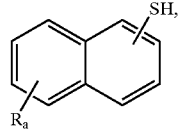

Ib wherein each of $Ak^1$ and $Ak^2$ is an optionally substituted alkyl group;
each R is a substituent; and
a is 0, 1, 2 or 3; or a derivative or salt thereof;
said method comprising contacting said phosphorus-deprotecting compound, derivative or salt, and a protected phosphorus-containing compound of formula II:

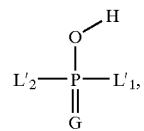

II wherein Ak is a phosphorus protecting group, e.g. an optionally substituted $C_1$–$C_{10}$ alkyl, G is O or S, and $L_1$ and $L_2$ are organic moieties optionally further comprising protected phosphorus moieties,
under conditions and for a period sufficient to remove Ak from the phosphorus-containing compound, thereby forming a deprotected compound of the formula:

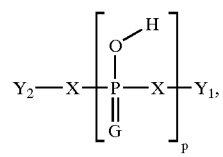

III wherein G, has the same meaning as in formula II,
$L'_1$ is $L_1$ or a phosphorus-deprotected analog thereof, and
$L'_2$ is $L_2$ or a phosphorus-deprotected analog thereof.

The foregoing and other needs are further met by embodiments of the present invention, which provide a process of making a compound of the formula:

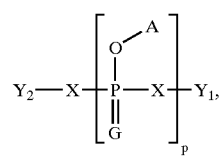

wherein each X is independently a nucleoside monomer or an analog thereof,
G is O or S,
$Y_1$ is H, a protecting group or a linking group conjugated to a support;
$Y_2$ is H, a protecting group or a linking group conjugated to a support, except that $Y_1$ and $Y_2$ cannot be simultaneously a linking group conjugated to a support;
p is a positive integer;
the process comprising contacting a phosphorus-protected compound of the formula:

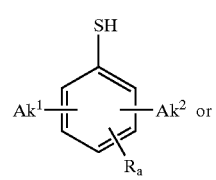

wherein A is a phosphorus protecting group,
with a phosphorus-deprotection compound of the formula Ia or Ib:

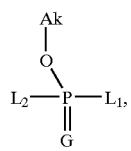

Ia

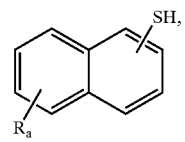

Ib wherein each of $Ak^1$ and $Ak^2$ is an optionally substituted alkyl group;
each R is independently a substituent; and
a is 0, 1, 2 or 3; or a salt or derivative thereof;
under conditions and for a period sufficient to remove A from the phosphorus-containing compound.

The foregoing and other needs are further met by embodiments of the present invention, which provide a process of deprotecting a phosphorus-protected oligonucleotide, the process comprising contacting said phosphorus-protected oligonucleotide with a deprotecting agent of formula Ia or Ib:

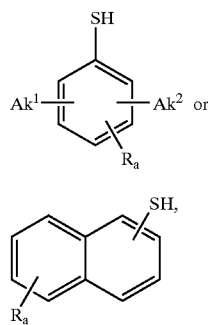

wherein each of $Ak^1$, $Ak^2$, R and a are as defined herein, for a time and under conditions sufficient to remove the phosphorus protecting group from the phosphorus-protected oligonucleotide.

Other aspects and advantages of the present invention will become apparent to the person skilled in the art upon consideration of the description of the invention and the appended claims.

DETAILED DESCRIPTION OF THE INVENTION

The herein-described invention provides a class of reagents for removal of phosphorus protecting groups from phosphorus-protected oligonucleotides and analogs thereof, methods of using members of such class of reagents for the removal of phosphorus protecting groups, and methods of oligonucleotide synthesis incorporating the use one or more members of such class of reagents in the synthetic methodology.

The present inventors have found that a class of reagents, herein referred to as phosphorus deprotecting reagent, are useful for the deprotection of phosphorus groups during oligonucleotide synthesis. This class of reagents is capable of removing alkyl protecting groups (e.g. methyl, ethyl, etc.) and do not require that the leaving group possess a β-electron withdrawing group. While not wishing to be bound by theory, the inventors theorize that the inventive phosphorus deprotecting reagents operate by direct nucleophilic attack on the α-carbon of the protecting group, rather than through the β-elimination route characterizing the cyanoethyl protecting group. The inventive class of reagents includes alkyl thiols and aryl thiols that do not possess offensive odors. Members of the inventive class of reagents are available from commercial sources in abundant quantities, have favorable toxicological properties, are non-malodorous and do not cause the formation of potentially reactive side products, such as acrylonitrile.

In some embodiments of the invention, the inventive phosphorus deprotecting compounds have a structure generically encompassed by formula Ia or Ib. It has been found that compounds having formula Ia or Ib possess the favorable characteristics of acceptable deprotecting times, lack of offensive odor and suitable solubility.

In some embodiments of the present invention, preferred reagents are of formulae Ia and Ib are those of formula Ia.

In particular embodiments, the inventive reagents are those of formula Ia, wherein at least one of $Ak^1$ and $Ak^2$ is a bulky alkyl group, such as the isopropyl group or the tert-butyl group. In some embodiments of the invention, one of the groups $Ak^1$ and $Ak^2$ is lower alkyl, such as methyl, and the other is a bulky alkyl group, such as isopropyl or tert-butyl. In especially notable embodiments, one of $Ak^1$ and $Ak^2$ is methyl, and the other is tert-butyl. In exemplary embodiments of the present invention, the reagent is 2-methyl-5-t-butylthiophenol. Other preferred embodiments include reagents of formula Ia that are non-malodorous.

The substituents R are generally selected from optionally substituted alkyl, optionally substituted cycloalkyl, optionally substituted aryl, SR", N(R")$_2$, OR", NHCOR", wherein each R" is independently H, alkyl, or substituted alkyl, or, where two R" groups are on a single N, the two R" groups together with the N to which they are bonded may form a cyclic group. Exemplary alkyl groups within the meaning of R are $C_1-C_{12}$ alkyl, for example methyl, ethyl, isopropyl, n-propyl, isobutyl, n-butyl, t-butyl, s-butyl, n-pentyl or dodecyl. Exemplary cycloalkyl groups are $C_3-C_{12}$ cycloalkyl, such as cyclopropyl, cyclobutyl or cyclohexyl. Exemplary aryl groups include phenyl, naphthyl, or p-methylphenyl. Exemplary R" groups include H, $C_1-C_{12}$ alkyl groups, such as, for example, methyl, ethyl, isopropyl, n-propyl, isobutyl, n-butyl, t-butyl, s-butyl, n-pentyl or dodecyl. Exemplary cyclic groups represented by N(R")$_2$ include piperidinyl, piperazinyl, N'-methylpiperazinyl, morpholino, thiomorpholino, homomorpholino and homothiomorpholino. Exemplary optional substituents include halo, NO$_2$, N(R''')$_2$, OR''', SR''', (where each R''' has the definition of R", above) or where R" is a cyclic group or forms a cyclic group, the substituent may be halo, alkyl, NO$_2$, cycloalkyl, aryl, N(R''')$_2$, OR''', or SR'''.

In some embodiments of the present invention, the value of a is 0 or 1.

The reagents and methods according to the present invention are well-suited to oligonucleotide synthesis, especially solid phase synthesis of phosphate and thiophosphate oligonucleotides.

The inventive class of phosphorus-deprotecting reagents should possess a soft nucleophilic character. Generally speaking, thiol functions possess such soft nucleophilic character, and thus the phosphorus-protecting groups of the present invention generally comprise at least one thiol group, or an equivalently soft nucleophile. Also, the phosphorus-deprotecting reagent according to the present invention is characterized by a lack of the foul odor typically possessed by thiophenol and other thiols. In general, the odor of the inventive phosphorus-deprotecting reagents from an entirely neutral odor (i.e. no discernable odor) to a mild kerosene like scent. In any case, a phosphorus-deprotecting reagent according to the present invention is unobjectionable to the olfactory senses of the ordinary person, and is hence considered non-malodorous. By non-malodorous, it is meant herein that the phosphorus-deprotecting reagent can be used on an industrial scale, e.g. on a scale suitable for deprotecting mmole, 10 mmole, 100 mmole, mole and larger quantities of oligonucleotide, without the necessity of using costly or complex odor-abatement equipment. This is in contrast to prior art thiol reagents, such as thiophenol, that have distinctive and irritating smells making them unsuitable for large scale oligonucleotide synthesis.

Exemplary phosphorus-deprotecting reagents are represented by formula Ia or Ib, described herein. As used in formulae Ia and Ib herein, substituents $Ak^1$ and $Ak^2$ are independently alkyl. In some embodiments $Ak^1$ and $Ak^2$ are $C_1$–$C_{10}$, branched or straight chain, alkyl. In some particular embodiments at least one of $Ak^1$ and $Ak^2$ is a lower alkyl, such as methyl, ethyl, isopropyl, n-propyl, isobutyl, n-butyl, s-butyl, t-butyl, 1,1-dimethylpropyl, etc. In some preferred embodiments, at least one of $Ak^1$ and $Ak^2$ is a bulky alkyl group, such as isopropyl, t-butyl or 1,1-dimethylpropyl. In some specific preferred embodiments, $Ak^1$ and $Ak^2$ are selected from methyl, ethyl, isopropyl, n-propyl, isobutyl, n-butyl, s-butyl and t-butyl and the other is selected from isopropyl, t-butyl and 1,1-dimethylpropyl. A particular inventive phosphorus-deprotecting compound within the scope of formula Ia is 2-methyl-5-t-butyl-thiophenol.

Exemplary optional substituents for alkyl (Ak, A, $R_5$, $R_6$, etc.) groups according to the present invention include halo (e.g. F, Cl, Br or I), nitro, nitroso, OH, SH, CN, optionally substituted phenyl, optionally substituted phenoxy, optionally substituted benzyloxy, heteroaryl, partially saturated heterocyclyl, fully saturated heterocyclyl and silyl.

A particular inventive phosphorus-deprotecting compound within the scope of formula Ib is 2-mercaptonaphthalene.

The compounds represented by formulae II and III are generally phosphorus-protected and phosphorus-deprotected oligonucleotides, respectively. Formula II represents an oligonucleotide before phosphorus-deprotection, and Formula III represents the same oligonucleotide after phosphorus-deprotection by an inventive phosphorus-deprotecting reagent. In their most general senses, Formulae II and III include not only oligonucleotides having pure phosphate or phosphorothioate backbones, but also those hybrid oligonucleotides comprising at least one phosphate or phosphorothioate linkage at least one other linkage between successive nucleosides or nucleoside analogs. It is thus to be understood that the phosphorus-deprotection methods according to the present invention are completely general and may be used to deprotect one or more phosphorus groups that are contained within a larger chemical entity.

In this regard, the term organic moiety as used in reference to $L_1$ and $L_2$ in formulae II and III, and elsewhere herein, includes one or more nucleotide moieties linked by phosphate or thiophosphate linking groups, i.e. oligomeric chains. $L_1$ and $L_2$ include structures that include one or more phosphate or thiophosphate nucleotide linkages, i.e. oligonucleotide chains, as well as one or more analogous structures, i.e. oligomeric chains. $L_1$ and $L_2$ may also independently comprise conjugated fatty acids, peptides, biotin, chitosan, or other groups used for various purposes, such as to enhance bioavailability of oligonucleotides for intracellular delivery.

For purposes of this invention, a structure that is analogous to a nucleotide includes a peptide nucleic acid (PNA), a locked nucleic acid (LNA), a morpholino nucleic acid, phosphoramidates, etc. Other examples are included herein.

In some embodiments of the invention, $L_1$ has the formula:

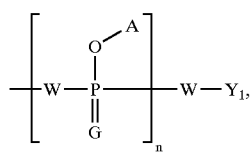

wherein each W is a monomeric nucleoside or nucleoside analog, each A is a phosphorus protecting group, each G is O or S, $Y_1$ is H, a protecting group or a linking group conjugated to a support, and n is zero or a positive integer.

In some embodiments of the invention, $L_2$ has the formula:

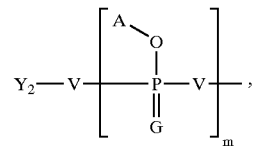

wherein each V is a monomeric nucleoside or an analog thereof, each A is a phosphorus protecting group, each G is O or S, $Y_2$ is H, a protecting group or a linking group conjugated to a support, and m is zero or a positive integer.

In some embodiments of the present invention, the oligonucleotide may be covalently linked, either directly or through an intervening linking group, to a solid support. In such cases, it is to be understood that only one end of the oligonucleotide can be bonded to the support at any one time. It is thus to be understood that in the context of the above description of L, and $L_2$, $Y_1$ and $Y_2$ cannot both simultaneously be a linking group conjugated to a support.

The integers n and m may have any positive value. In some embodiments of the invention, the sum of n and m is in the range of zero to 80. In exemplary embodiments of the invention, the sum of n and m is in the range of about 6 to about 60, in particular from about 12 to about 30, and more particularly in the range of about 15 to about 25. Particular values of n+m are 17, 18, 19, 20, 21 and 22.

The monomeric nucleoside moieties or analogs thereof include naturally occurring nucleosides (i.e. ribonucleosides and 2'-deoxynucleosides), 2'-modified nucleosides, locked nucleosides, sugar-modified, base modified, erythro-, arabino- and other modified nucleosides as further described herein.

In general, a modified nucleoside may differ from a naturally occurring nucleoside in the sugar ring, in the base, in substituents on the sugar ring, substituents on the base, or in a combination of these elements.

In general, the terms "sugar" and "sugar analog" include the naturally-occurring β-D-ribose sugars, and 2'-deoxy-β-D-ribose sugars, the analogous erythrose and arabinose sugars, and substituted variants thereof. The term "sugar analog" also includes cyclic moieties that function like the naturally occurring sugars, such as morpholino structures, as described herein. In some embodiments of the present invention, the sugar or sugar analog may have the formula W or V:

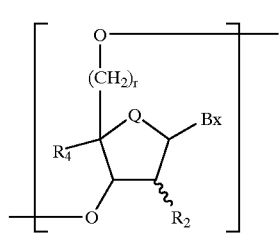

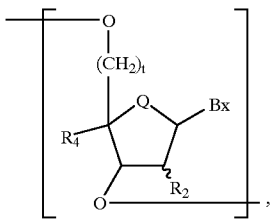

wherein Q is O, S, NH, NR$_5$, CH$_2$, CHR$_5$ or CR$_5$R$_6$, wherein each of R$_5$ and R$_6$ is F, an optionally substituted alkyl group, or R$_5$ and R$_6$ together form a spiro ring with the carbon to which they are attached, B$_x$ is a nucleobase, R$_2$ is H, OH, or a 2'-substituent and R$_4$ is H, or R$_2$ and R$_4$ together form a bridge, such as 2'O—(CH$_2$)$_q$-4', or 2'-(CH$_2$)$_q$-4', wherein q is 1 or 2; or R$_2$ and R$_4$ together form a bridge 2'-CH$_2$—O—CH$_2$-4'; and r and t are each independently 0 or 1.

As depicted in W and V above, the 2'-position of the sugar moiety may be unsubstituted (i.e. 2'-deoxy), or substituted with a sugar substituent known in the art, such as 2'-O-methyl, 2'-O-methoxyethyl, etc., as described in more detail herein.

Although some preferred embodiments of the present invention are oligonucleotides (including oligonucleotides comprising phosphorothioate nucleotide linkages), other embodiments of the invention may be oligomeric hybrids. In some embodiments of the invention, L$_1$ and L$_2$ may have similar or different backbones. For example, L$_1$ may have a PNA backbone, while L$_2$ may have a phosphate or phosphorothioate backbone, or vice versa. In other exemplary embodiments, L$_1$ may comprise a phosphoramidate backbone, while L$_2$ comprises an oligonucleotide backbone. Other hybrids are also contemplated within the term "organic moiety".

As used herein a sugar substituent is a substituent that is covalently attached to a position of the sugar moiety. Oligomeric compounds of the present invention may incorporate sugar moieties modified with sugar substituents to enhance one or more properties, such as nuclease resistance or binding affinity. The 2'-position has been a preferred position for covalent attachment of sugar substituents. However, the 3' and 5' positions and the heterocyclic base moiety of selected nucleosides have also been modified with sugar substituents. In particular, as described herein, the 2'- and 4'-positions may be joined by a divalent group that forms a bridge. Such a sugar unit is referred to as a "locked nucleic acid" (LNA), as described in more detail herein.

A representative list of sugar substituents useful in the present invention includes H (i.e. deoxy), —OH, SH, alkyl, alkenyl, alkynyl, aryl, alkoxy, substituted alkoxy, alkenyloxy, substituted alkenyloxy, alkynyloxy, substituted alkynyloxy, aminoalkoxy, alkoxyalkoxy, alkylaminoalkoxy, imidazolylalkoxy, alkenylthio, alkynylthio, alkenylamino, alkynylamino, aryloxy, arylthio, aralkyloxy, aralkylthio, aralkylamino, N-phthalimido, halogen (e.g. fluoro), —C(=O)—R (wherein R is an organic radical), carboxyl, nitro, nitroso, cyano, trifluoromethyl, trifluoromethoxy, imidazolyl, azido, hydrazino, aminooxy, isocyanato, isothiocyanato, sulfoxide (—S(=O)—R), sulfone (—S(=O)$_2$—R (wherein R is an organic radical)), disulfide (—S—S—R (wherein R is an organic radical)), silyl, a heterocycle, a carbocycle, an intercalator, a reporter group, conjugate, polyamine, polyamide, polyalkylene glycol, and polyethers of the formula (O-alkyl)$_m$, where m is 1 to about 10. As used herein "sugar substituent" includes modifications (such as replacement of a hydroxyl with a hydrogen, i.e. deoxy modification), as well as modifications on the sugar hydroxy (wherein the H of the hydroxyl group is replaced by a substituent other than H), and modifications in which the sugar hydroxyl group is replaced with a group in which oxygen is not bonded to the sugar ring (see e.g. SH, NH$_2$, etc. herein). Suitable sugar modifications are described more fully herein.

Where R$^2$ and R$^4$ together form a bridge, such as 2'-O—(CH$_2$)$_q$-4' (q is 1 or 2), 2'-O—(CH$_2$)$_q$-4' (q is 1 or 2), or 2'-CH$_2$—O—CH$_2$-4', the sugar analog is termed a locked-nucleic acid (LNA). The linkage may be a methelyne (—CH$_2$—)$_n$ group bridging the 2' oxygen atom and the 4' carbon atom wherein n is 1 or 2 (Singh et al., Chem. Commun., 1998, 4, 455–456). See also U.S. Pat. No. 6,268,490, which is expressly incorporated herein by reference. LNA and LNA analogs display very high duplex thermal stabilities with complementary DNA and RNA (Tm=+3 to +10 C), stability towards 3'-exonucleolytic degradation and good solubility properties.

Novel types of LNA-modified oligonucleotides, as well as the LNAs, are useful in a wide range of diagnostic and therapeutic applications. Among these are antisense applications, PCR applications, strand-displacement oligomers, substrates for nucleic acid polymerases and generally as nucleotide based drugs.

Potent and nontoxic antisense oligonucleotides containing LNAs have been described (Wahlestedt et al., Proc. Natl. Acad. Sci. U.S.A., 2000, 97, 5633–5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607–3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219–2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035–10039). In addition, 2'-Amino- and 2'-methylamino-LNA's have been prepared and the thermal stability of their duplexes with complementary RNA and DNA strands has been previously reported.

Some preferred sugar modifications include hydrogen (e.g. 2'-deoxy), a hydroxyl protected by a protecting group, hydroxyl in which the H of the OH group has been replaced by substituted or unsubstituted alkyl, alkenyl or alkynyl (wherein the substituent groups are selected from hydroxyl, amino, alkoxy, carboxyl, benzyl, phenyl, nitro, thiol, thioalkoxy, halogen, alkyl, aryl, alkenyl and alkynyl). Further representative substituent groups are disclosed in U.S. Pat. No. 5,212,295, at column 12, lines 41–50, hereby incorporated by reference in its entirety.

Additional sugar modifications amenable to the present invention include those in which the 2'-hydroxyl group has been replaced by 2'-SR or 2'-N(R)$_2$. Some 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., J. Org. Chem., 1997, 62, 3415–3420. 2'-N(R)$_2$ nucleosides are disclosed by Goettingen, M., J. Org. Chem., 1996, 61, 6273–6281; and Polushin et al., Tetrahedron Lett., 1996, 37, 3227–3230.

Preferred polyethers are linear and cyclic polyethylene glycols (PEGs), and (PEG)-containing groups, such as crown ethers and those which are disclosed by Ouchi et al. (*Drug Design and Discovery* 1992, 9, 93), Ravasio et al. (J. Org. Chem. 1991, 56, 4329) and Delgardo et. al. (Critical Reviews in Therapeutic Drug Carrier Systems 1992, 9, 249), each of which is herein incorporated by reference in its entirety. Further sugar modifications are disclosed in Cook, P. D., Anti-Cancer Drug Design, 1991, 6, 585–607. Fluoro, O-alkyl, O-alkylamino, O-alkylimidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Further representative substituent groups include groups of formula IX or X:

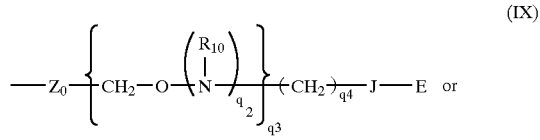

(IX)

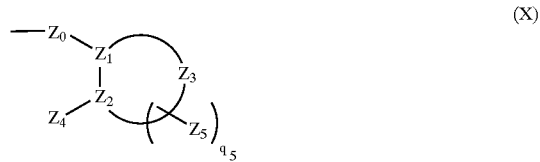

(X)

wherein:
Z$_0$ is O, S or NH;

J is a single bond, O or C(=O);
E is C$_1$–C$_{10}$ alkyl, N(R$_{15}$)(R$_{16}$), N(R$_{15}$)(R$_{17}$), N=C(R$_{5a}$)(R$_{6a}$), N=C(R$_{5a}$) (R$_{7a}$) or has formula:

(XI)

each R$_{17}$, R$_8$, R$_9$, R$_{11}$ and R$_{12}$ is, independently, hydrogen, C(O)R$_{13}$, substituted or unsubstituted C$_1$–C$_{10}$alkyl, substituted or unsubstituted C$_2$–C$_{10}$ alkenyl, substituted or unsubstituted C$_2$–C$_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;
or optionally, R$_{11}$, and R$_{12}$, together form a phthalimido moiety with the nitrogen atom to which they are attached;

each R$_{13}$ is, independently, substituted or unsubstituted C$_1$–C$_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;
R$_{10}$ is T-L,
T is a bond or a linking moiety;
L is a chemical functional group, a conjugate group or a solid support material;
each R$_{15}$ and R$_{16}$ is, independently, H, a nitrogen protecting group, substituted or unsubstituted C$_1$–C$_{10}$alkyl, substituted or unsubstituted C$_2$–C$_{10}$alkenyl, substituted or unsubstituted C$_2$–C$_{10}$alkynyl, wherein the substituent groups are selected from hydroxyl, amino, alkoxy, carboxy, benzyl, phenyl, nitro, thiol, thioalkoxy, halogen, alkyl, aryl, alkenyl and alkynyl or R$_{15}$ and R$_{16}$, together, are a nitrogen protecting group or are joined in a ring structure that optionally includes an additional heteroatom selected from N and O or a chemical functional group;
each R$_{5a}$ and R$_{6a}$ is, independently, H, substituted or unsubstituted C$_1$–C$_{10}$alkyl, substituted or unsubstituted C$_2$–C$_{10}$alkenyl, or unsubstituted C$_2$–C$_{10}$alkynyl, wherein the substituent groups are selected from hydroxyl, amino, alkoxy, carboxy, benzyl, phenyl, nitro, thiol, thioalkoxy, halogen, alkyl, aryl, alkenyl and alkynyl. Further representative alkyl substituents are disclosed in U.S. Pat. No. 5,212,295, at column 12, lines 41–50, hereby incorporated by reference in its entirety.
R$_{7a}$ is -T-L;
Z$_4$ is OM, SM, or N(M)$_2$;
each M is, independently, H, C$_1$–C$_8$ alkyl, C$_1$–C$_8$ haloalkyl, C(=NH)N(H)R$_{26}$, C(=O)N(H)R$_{26}$ or OC(=O)N(H)R$_{26}$;
R$_{26}$ is H or C$_1$–C$_8$ alkyl;
Z$_1$, Z$_2$ and Z$_3$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;
Z$_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N(R$_{15}$)(R$_{16}$) OR$_{15}$, halo, SR$_{15}$ or CN;
each q$_2$ is, independently, 0 or 1;
q$_3$ is 0 or an integer from 1 to 10;
q$_4$ is an integer from 1 to 10;
q$_5$ is from 0, 1 or 2; and
provided that when q$_3$ is 0, q$_4$ is greater than 1.

Representative substituents of Formula IX are disclosed in U.S. Pat. No. 6,172,209, hereby incorporated by reference in its entirety.

Representative cyclic substituent groups of Formula X are disclosed in U.S. Pat. No. 6,271,358, hereby incorporated by reference in its entirety.

Particularly preferred sugar substituent groups include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$ and O(CH$_2$)$_n$ON [(CH$_2$)$_n$CH$_3$)]$_2$, where n and m are from 1 to about 10 and each of the groups replaces an OH group of the sugar moiety.

Some preferred oligomeric compounds of the invention contain at least one nucleoside having one of the following substituent groups: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O CH$_2$CH$_2$OCH$_3$, also known as 2'-O-(2-methoxyethyl) or 2'-MOE] (Martin et al., Helv. Chim. Acta, 1995, 78, 486), i.e., an alkoxyalkoxy group. A further preferred modification is 2'-dimethylaminooxyethoxy, i.e., a O(CH$_2$)$_2$ON(CH$_3$)$_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, entitled "Aminooxy-Functionalized Oligomers and Methods for Making Same;" hereby incorporated by reference in their entirety.

Other preferred modifications include 2'-deoxy-2'-methoxy (i.e. the 2'-OH is replaced with a 2'-O—CH$_3$), 2'-deoxy-2'-aminopropoxy (2'-OCH$_2$CH$_2$CH$_2$NH$_2$) and 2'-deoxy-2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'–5' linked oligomer and at the 5' position of a 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Representative guanidino substituent groups that are shown in formula XI are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200, hereby incorporated by reference in its entirety.

Representative dimethylaminoethyloxyethyl substituent groups are disclosed in U.S. Pat. No. 6,043,352 and in International Patent Application PCT/US99/17895, entitled "2'-O-Dimethylaminoethyloxyethyl-Modified Oligonucleotides", filed Aug. 6, 1999, hereby incorporated by reference in their entirety.

In some embodiments of the present invention, the 2'-substituent is 2'-SH, 2'-aminoalkyloxyalkoxy (see U.S. Pat. No. 6,127,533 and U.S. Ser. No. 09/370,625, filed Aug. 6, 1999, each incorporated herein by reference in its entirety), 2'-aminooxy substituents (see U.S. Ser. No. 09/370,541, filed Aug. 9, 1999, incorporated herein by reference in its entirety), aminooxy substituents (see U.S. Ser. No. 09/344,260, filed Jun. 25, 1999, incorporated herein by reference in its entirety), a substituent —X$_1$—Y$_1$, wherein X$_1$ is O, S, NR, CR$_2$ (R is alkyl) and Y$_1$ is substituted or unsubstituted alkyl, alkenyl, aryl (substituents are OH, NH$_2$, SH, COOH, amido, ester, aminoalkylamido, Si(alkyl)$_3$ or a drug moiety (see U.S. Pat. No. 5,466,786 and U.S. Pat. No. 5,792,847, each incorporated by reference in its entirety), 2-O—X$_2$, wherein X$_2$ is substituted alkyl, and the substituent is O-alkyl, S-alkyl, NH-alkyl, N-dialkyl, O-aryl, S-aryl, NH-aralkyl, O-aralkyl, S-aralkyl or NH-aralkyl (See U.S. Pat. No. 5,914,396, incorporated herein in its entirety), 2'-F (see U.S. Pat. No. 5,955,589, incorporated herein in its entirety), 2'-alkylsulfonyl, 2'-alkylsulfinyl (see U.S. Pat. No. 5,859,221, incorporated herein in its entirety), 2'-aminoalkyloxy or 2'-imidazolylalkyloxy (see U.S. Pat. No. 5,872,232, incorporated herein in its entirety), bromo, chloro, iodo, azido, amino, substituted amino, bromomethyl, chloromethyl, iodomethyl, cyanato, bromoalkoxy, chloroalkoxyl, iodalkoxyl, alkyl sulfide, alkyl sulfonate, nitrate or nitrite per Cook et al., U.S. Pat. No. 6,307,040, incorporated herein by reference, 2'-O-alkyl or 2'-fluoro per Bennett et al., U.S. Pat. No. 5,703,054, 2'-allyl or azido as taught by U.S. Ser. No. 09/389,283, filed Sep. 2, 1999, 2'-carbamates and 2'-amides as taught by U.S. Pat. No. 6,322,987, 2'-aminocarbonylalkoxy per U.S. Pat. No. 6,147,200, each of the foregoing patents and patent applications being expressly incorporated herein in their entireties.

In some embodiments of the present invention, $R^2$ may be in a configuration other than the ribo-configuration (i.e. $R^2$ bound to sugar ring by a down-bond). Such configurations include the arabino-configuration ($R^2$ bound to the sugar ring by an up-bond).

Arabino-pentofuranosyl nucleotide building blocks have been described. (Damha et. al., J.A.C.S., 1998, 120, 12976–12977 and Damha et. al., Bioconjugate Chem., 1999, 10, 299–305). The arabino-pentofuranosyl oligonucleotides, i.e., arabinonucleic acids, described by Damha et. al., utilized either arabinose or 2'-deoxy-2'-fluoro arabinose as the sugar unit of their respective nucleotides. In one of the two arabinonucleic acids described, all of the nucleotides of the nucleic acid were arabinose and in the other, all of the nucleotides were 2'-deoxy-2'-fluoro arabinose. In both of these nucleic acids, the nucleotides were joined via phosphodiester linkages. The 2'-fluoro arabino-containing oligonucleotides, when bound to RNA, activate cleavage of the RNA by E. coli and HIV-RT RNase H. While the two arabinonucleic acids were more stable to serum and cellular nucleases than DNA, they were less stable than normal phosphorothioate deoxyoligonucleotides.

The inclusion of certain substituents in the foregoing description is not intended to limit the meaning of the meaning of sugar or of a sugar analog. The present invention is generally applicable to any phosphorus-protected oligonucleotide, and in general the particular sugar or analog thereof will not be critical to the success of the described reagents or methods.

It is not necessary for all positions in a given oligomeric compound to be uniformly modified, and in fact more than one of the aforementioned modifications may be incorporated in a single oligomeric compound or even at a single monomeric subunit such as a nucleoside within an oligomeric compound. The present invention also includes oligomeric compounds which are chimeric compounds. "Chimeric" oligomeric compounds or "chimeras," in the context of this invention, are oligomeric compounds which contain two or more chemically distinct regions, each made up of at least one monomer unit, i.e., a nucleotide in the case of an oligonucleotide compound. These oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, modified oligonucleotides, oligonucleotide analogs, oligonucleosides and/or oligonucleotide mimetics as described above. Such compounds have also been referred to in the art as hybrids hemimers, gapmers or inverted gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

Some embodiments of the present invention provide oligomeric compounds comprising a plurality of linked nucleosides wherein the preferred internucleoside linkage is a 3',5'-linkage. Alternatively, 2',5'-linkages can be used (as described in U.S. application Ser. No. 09/115,043, filed Jul. 14, 1998). A 2',5'-linkage is one that covalently connects the 2'-position of the sugar portion of one nucleotide subunit with the 5'-position of the sugar portion of an adjacent nucleotide subunit.

The term "nucleobase" is used herein to indicate a naturally occurring nucleic acid base moiety as well as bases having ring substituents and/or ring replacements. The term "nucleobase" has also been called a "heterocyclic base moiety" or simply a "base" in the art). Nucleobase moieties amenable to the present invention includes both naturally and non-naturally occurring nucleobases. The nucleobase moiety further may be protected wherein one or more functionalities of the base bears a protecting group. As used herein, "unmodified" or "natural" nucleobases include the purine bases adenine and guanine, and the pyrimidine bases thymine, cytosine and uracil. Modified nucleobases include other synthetic and natural nucleobases such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substitut adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the Concise Encyclopedia Of Polymer Science And Engineering, pages 858–859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289–302, Crooke, S. T. and Lebleu, B., ed., CRC Press, 1993.

Certain heterocyclic base moieties are particularly useful for increasing the binding affinity of the oligomeric compounds of the invention to complementary targets. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with selected 2'-sugar modifications such as 2'-methoxyethyl groups.

Representative United States patents that teach the preparation of heterocyclic base moieties (modified nucleobases) include, but are not limited to, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, certain of which are commonly owned, and each of which is herein incorporated by reference, and commonly owned U.S. patent application Ser. No. 08/762,587, filed on Dec. 10, 1996, also herein incorporated by reference.

In some embodiments of the present invention, oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

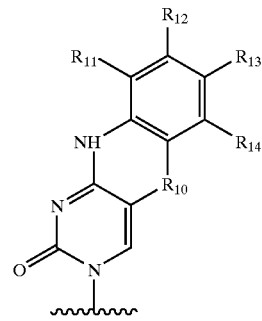

Representative cytosine analogs that make 3 hydrogen bonds with a guanosine in a second strand include 1,3-diazaphenoxazine-2-one ($R_{10}$—O, $R_{11}$—$R_{14}$=H) [Kurchavov, et al., *Nucleosides and Nucleotides*, 1997, 16, 1837–1846], 1,3-diazaphenothiazine-2-one ($R_{10}$=S, $R_{11}$—$R_{14}$=H), [Lin, K.-Y.; Jones, R. J.; Matteucci, M. J. Am. Chem. Soc. 1995, 117, 3873–3874] and 6,7,8,9-tetrafluoro-1,3-diazaphenoxazine-2-one ($R_{10}$=O, $R_{11}$—$R_{14}$=F) [Wang, J.; Lin, K.-Y., Matteucci, M. Tetrahedron Lett. 1998, 39, 8385–8388]. Incorporated into oligonucleotides these base modifications were shown to hybridize with complementary guanine and the latter was also shown to hybridize with adenine and to enhance helical thermal stability by extended stacking interactions.

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) [Lin, K.-Y.; Matteucci, M. J. Am. Chem. Soc. 1998, 120, 8531–8532]. Binding studies demonstrated that a single incorporation could enhance the binding affinity of a model oligonucleotide to its complementary target DNA or RNA with a $\Delta T_m$ of up to 18° relative to 5-methyl cytosine ($dC5^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to $dC5^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety. Such compounds include those having the formula:

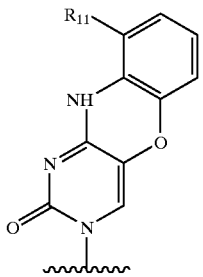

Wherein $R_{11}$ includes $(CH_3)_2N$—$(CH_2)_2$—O—; $H_2N$—$(CH_2)_3$—; Ph-$CH_2$—O—C(=)—N(H)—$(CH_2)_3$—; $H_2N$—; Fluorenyl-$CH_2$—O—C(=O)—N(H)—$(CH_2)_3$—; Phthalimidyl-$CH_2$—O—C(=O)—N(H)—$(CH_2)_3$; Ph-$CH_2$—O—C(=O)—N(H)—$(CH_2)_2$—O—; Ph-$CH_2$—O—C(=O)—N(H)—$(CH_2)_3$—O—; $(CH_3)_2N$—N(H)—$(CH_2)_2$—O—; Fluorenyl-$CH_2$—O—C(=O)—N(H)—$(CH_2)_2$—O—; Fluorenyl-$CH_2$—O—C(=O)—N(H)—$(CH_2)_3$—O—; $H_2N$—$(CH_2)_2$—O—$CH_2$—; $N_3$—$(CH_2)_2$—O—$CH_2$—; $H_2N$—$(CH_2)_2$—O—, and $NH_2C$(=NH)NH—.

Also disclosed are tricyclic heterocyclic compounds of the formula:

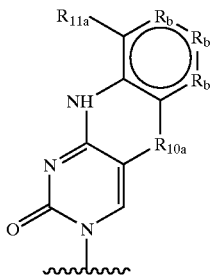

Wherein
$R_{10a}$ is O, S or N—$CH_3$;
$R_{11a}$ is $A(Z)_{x1}$, wherein A is a spacer and Z independently is a label bonding group bonding group optionally bonded to a detectable label, but $R_{11a}$ is not amine, protected amine, nitro or cyano;

X1 is 1, 2 or 3; and $R_b$ is independently —CH=, —N=, —C($C_{1-8}$ alkyl)=or —C(halogen)=, but no adjacent $R_b$ are both —N=, or two adjacent $R_b$ are taken together to form a ring having the structure:

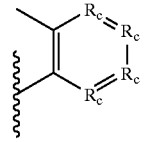

where $R_c$ is independently —CH=, —N=, —C($C_{1-8}$ alkyl)=or —C(halogen)=, but no adjacent $R_b$ are both —N=.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K.-Y.; Matteucci, M. J. Am. Chem. Soc. 1998, 120, 8531–8532]. The activity enhancement was even more pronounced in case of G-clamp, as a single substitution was shown to significantly improve the in vitro potency of a 20mer 2'-deoxyphosphorothloate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513–3518]. Nevertheless, to optimize oligonucleotide design and to better understand the impact of these heterocyclic modifications on the biological activity, it is important to evaluate their effect on the nuclease stability of the oligomers.

Further tricyclic and tetracyclic heteroaryl compounds amenable to the present invention include those having the formulas:

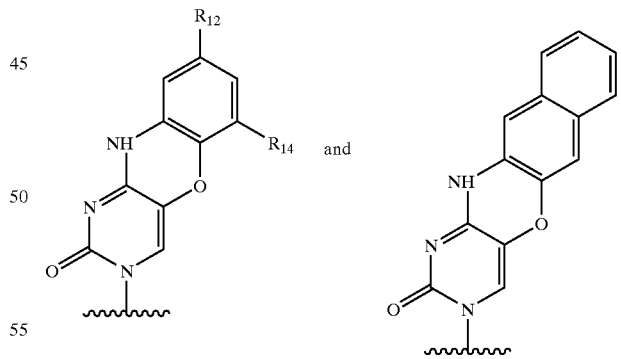

wherein $R_{14}$ is $NO_2$ or both $R_{14}$ and $R_{12}$ are independently —$CH_3$. The synthesis of these compounds is dicslosed in U.S. Pat. No. 5,434,257, which issued on Jul. 18, 1995, U.S. Pat. No. 5,502,177, which issued on Mar. 26, 1996, and U.S. Pat. No. 5,646,269, which issued on Jul. 8, 1997, the contents of which are commonly assigned with this application and are incorporated herein in their entirety.

Further tricyclic heterocyclic compounds amenable to the present invention also disclosed in the "257, 177 and 269" Patents include those having the formula:

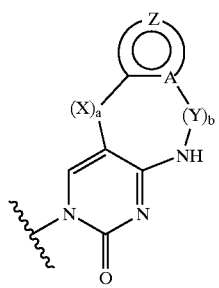

a and b are independently 0 or 1 with the total of a and b being 0 or 1;

A is N, C or CH;

X is S, O, C=O, NH or NCH$_2$, R$^6$;

Y is C=O;

Z is taken together with A to form an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a C atom, 2 N ring heteroatoms separated by a carbon atom, or 3 N ring heteroatoms at least 2 of which are separated by a carbon atom, and wherein the aryl or heteroaryl ring carbon atoms are unsubstituted with other than H or at least 1 non-bridging ring carbon atom is substituted with R$^{20}$ or =O;

or Z is taken together with A to form an aryl ring structure comprising 6 ring atoms wherein the aryl ring carbon atoms are unsubstituted with other than H or at least 1 nonbridging ring carbon atom is substituted with R$^6$ or =O;

R$^6$ is independently H, C$_{1-6}$ alkyl, C$_{2-6}$ alkenyl, C$_{2-6}$ alkynyl, NO$_2$, N(R$^3$)$_2$, CN or halo, or an R$^6$ is taken together with an adjacent Z group R$^6$ to complete a phenyl ring;

R$^{20}$ is, independently, H, C$_{1-6}$ alkyl, C$_{2-6}$ alkyl, C$_{2-6}$ alkenyl, C$_{2-6}$ alkynyl, NO$_2$, N(R$^{21}$)$_2$, CN, or halo, or an R$^{20}$ is taken together with an adjacent R$^{20}$ to complete a ring containing 5 or 6 ring atoms, and tautomers, solvates and salts thereof;

R$^{21}$ is, independently, H or a protecting group;

R$^3$ is a protecting group or H; and tautomers, solvates and salts thereof.

More specific examples included in the "257, 177 and 269" Patents are compounds of the formula:

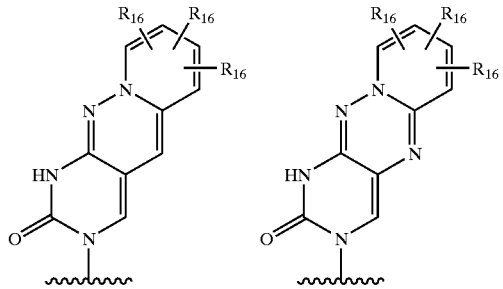

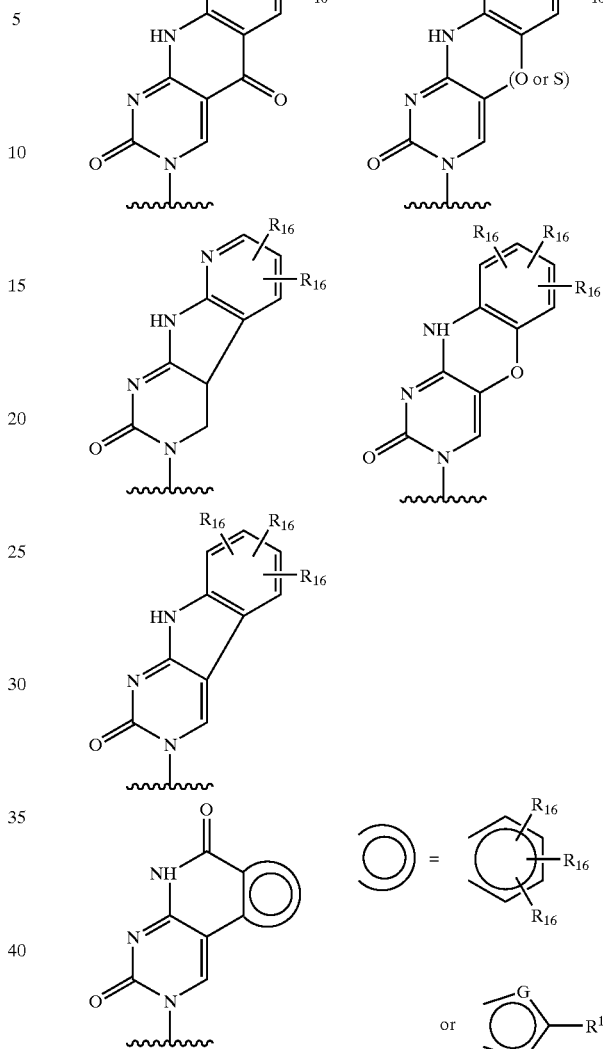

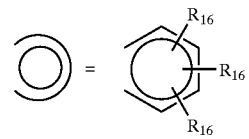

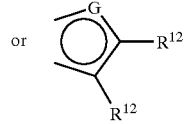

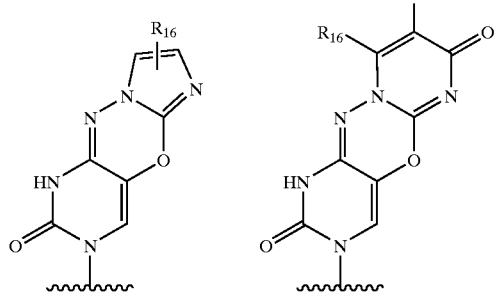

wherein each R$_{16}$, is, independently, selected from hydrogen and various substituent groups.

The recitation of certain nucleobases in the foregoing description is not intended to limit the interpretation of the meaning of nucleobase. The skilled artisan will recognize that the present invention is directed toward reagents and methods for deprotecting a phosphorus group, and the particular base or bases included in the phosphorus-protected oligonucleotide are not generally critical to the success of the invention.

As the phosphorus protecting groups described herein are those protecting groups that may be removed by direct nucleophilic substitution of a phosphorus-deprotecting reagent's nucleophilic center (e.g. the sulfur of a mercapto or thiol moiety) for the oxygen of the phosphate or phosphorothioate moiety. Known phosphorus protecting groups may be used in accordance with the present invention. Such protecting groups are disclosed, for instance, in the Caruthers and Köster patents cited herein as well as (list all the Ravikumar patents), all of which are incorporated by reference.

While the cyanoethyl and other β-eliminable groups can be used as phosphorus protecting groups in accordance with the present invention, it is generally unnecessary that the phosphorus protecting group possess a β-electron withdrawing group such as CN. Indeed, one of the advantages of the reagents and methods according to the present invention is that a simple alkyl phosphorus protecting group may be used instead of the more costly cyanoethyl group. However, another advantage of the present invention is that the inventive phosphorus-deprotecting reagent can be used with a variety of phosphorus protecting groups, provided that they are amenable to direct substitution of the phosphorus-protecting group's nucleophile for the phosphate or phosphorothioate oxygen on the phosphorus protecting group. This reaction is demonstrated schematically below:

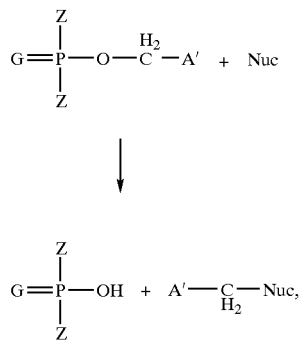

wherein G is O or S, each Z is an organic moiety, A' is the residue of a phosphorus protecting group, and Nuc is a nucleophile, such as a thiol group.

As can be seen, it is generally not critical to the inventive method whether there is a substituent on the β-position of the phosphorus protecting group, so long as the phosphorus-protecting group remains available for an SN1-type nucleophilic substitution. Nonetheless, as alkyl-protected phosphorus moieties are generally commercially available, and as the alkyl-protected phosphorus moieties are generally simpler in structure, the alkyl-protected phosphorus is preferred for use in accordance with the present invention.

Accordingly, the phosphorus-protecting groups may be alkyl groups, such as methyl or ethyl, taught by Caruthers et al., U.S. Pat. No. 4,458,066; cyanoalkyl groups, such as cyanoethyl, taught by Köster et al, U.S. Pat. No. Re. 34,069; silylalkyl groups, such as those taught by Ravikumar et al. U.S. Pat. No. 5,847,106, U.S. Pat. Nos. 6,124,450, 5,614,621, 5,847,106; an optionally substituted alkenyl such as those taught by Ravikumar et al., U.S. Pat. No. 5,705,621, U.S. Pat. No. 6,051,699; arylcarbonyloxyalkyl, arylthiocarbonyloxyalkyl, arylcarbonylaminoalkyl, arylthiocarbonylaminoalkyl, aryloxycarbonyloxyalkyl, aryloxythio-carbonyloxyalkyl, aryloxycarbonylaminoalkyl, aryloxythiocarbonyl-aminoalkyl, arylthiocarbonyloxyalkyl, arylthiothiocarbonyloxyalkyl, arylthiocarbonylaminoalkyl, arylthiothiocarbonylamino-alkyl, all as disclosed in Guzaev et al., U.S. Pat. No. 6,121,437; carbonylaminoalkyl, such as those taught in Cheruvallath et al., U.S. Pat. No. 5,760,209, U.S. Pat. No. 5,783,690; aralkyl as taught by Yau, U.S. Pat. No. 5,210,264; substituted aralkyl, such as those discussed in Capaldi et al., U.S. Pat. No. 6,020,475, U.S. Pat. No. 6,160,152; optionally substituted alkenyl, such as those disclosed by Manoharan in U.S. Pat. No. 6,169,177; substituted aryloxyalkyl or arylthioalkyl as taught by Cheruvallath et al., U.S. Pat. No. 6,326,478, each of which is expressly incorporated herein by reference.

In preferred embodiments of the invention, the phosphorus protecting group is alkyl, preferably $C_1$–$C_{10}$ alkyl, and even more preferably $C_1$–$C_5$ alkyl. Where the alkyl phosphorus protecting group is $C_3$ or higher, it may be branched. One preferred alkyl phosphorus protecting group is methyl. Another preferred alkyl phosphorus protecting group is ethyl. Alkyl-protected phosphitylating agents are described, for instance, in the Caruthers patents, cited herein, which are expressly incorporated by reference.

The term "phosphorus-deprotected analog" of $L_1$ or $L_2$ as used in regard to formula III, and elsewhere herein, indicates that the protecting group has been removed and a free POH (or, depending upon the pH of the solution in which the oligonucleotide is dissolved, PO⁻) moiety has been produced from an analogous PO-Ak species. Thus, the terminology "phosphorus-deprotected analog" is used to denote those species that one of skill in the art would recognize would be produced upon interaction of the inventive deprotecting reagents with one or more protected phosphorus groups in the $L_1$ and/or $L_2$ organic moieties. Thus, where $L_1$, $L_2$ or both comprise protected phosphorus groups, $L'_1$, and $L'_2$ indicate that deprotection of some or all of the protected phosphorus groups, preferably all the phosphorus groups, in $L_1$ and/or $L_2$ has taken place. In some cases, phosphorus-deprotection may be incomplete, and this case also is included within the meaning of "phosphorus-deprotected analog" as embraced by $L_1$ and $L_2$.

The term "protecting group" as used in reference to $Y_1$ and $Y_2$ herein includes 5'- and 3'-protecting groups. $Y_1$ may be stable under basic conditions but acid-labile. A wide variety of protecting groups can be employed in the methods of the invention. In general, protecting groups render chemical functionality inert to specific reaction conditions and can be appended to and removed from such functionality in a molecule. Representative protecting groups are disclosed by Beaucage et al. in Advances in Synthesis of Oligonucleotides by the Phosphoramidite Approach, Tetrahedron, 1992, 48, 2223–2311. Preferred protecting groups include 4,4'-dimethoxytriphenylmethyl (DMT), which is base stable and acid-labile. Other 5'-protecting groups include monomethoxytrityl, 9-phenylxanthen-9-yl (Pixyl) and 9-(p-methoxyphenyl) xanthen-9-yl (Mox). See U.S. Pat. No. 6,211,350, incorporated herein by reference, for further discussion of 5'-protecting groups.

$Y_2$ may be a linker to a solid support or a hydroxyl protecting group for the 3'-function of a nucleoside. When $Y_2$ is a hydroxyl protecting group, it will generally be stable under acid conditions, or at least under conditions under which $Y_1$ is generally labile. Exemplary protecting groups include acyl protecting groups, such as acetyl or levulinyl. Other useful 3'-protecting groups are discussed by Beaucage et al. and U.S. Pat. No. 6,211,350, cited above.

In any case, $Y_1$ and $Y_2$ are generally removed under different conditions. For example, it is generally useful for $Y_1$ to be acid-labile and base-stable, while $Y_2$ is acid-labile and base-stable, or vice versa.

The current method of choice for the preparation of oligomeric compounds utilizes support media. Support media is used for attachment of a first nucleoside or other synthon which is then iteratively elongated to give a final oligomeric compound or other polymer such as a polypeptide. Support media can be selected to be insoluble or have variable solubility in different solvents to allow the growing support bound polymer to be either in or out of solution as desired. Traditional support media such as solid supports are for the most part insoluble and are routinely placed in a reaction vessel while reagents and solvents react and or wash the growing chain until cleavage the final polymeric compound. More recent approaches have introduced soluble supports including soluble polymer supports to allow precipitating and dissolving the iteratively synthesized product at desired points in the synthesis (Gravert et al., Chem. Rev., 1997, 97, 489–510).

The term support media is intended to include all forms of support known to the art skilled for the synthesis of oligomeric compounds and related compounds such as peptides. Some representative support media that are amenable to the methods of the present invention include but are not limited to the following: controlled pore glass (CPG); oxalyl controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl] propylsilane and porous glass beads (see Parr and Grohmann, *Angew. Chem. Internal. Ed.* 1972, 11, 314, sold under the trademark "PORASIL E" by Waters Associates, Framingham, Mass., USA); the mono ester of 1,4-dihydroxymethylbenzene and silica (see Bayer and Jung, *Tetrahedron Lett.*, 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support media, polyethylene glycol PEG's (see Bonora et al., Organic Process Research & Development, 2000, 4, 225–231).

Further support media amenable to the present invention include without limitation PEPS support a polyethylene (PE) film with pendant long-chain polystyrene (PS) grafts (molecular weight on the order of $10^6$, (see Berg, et al., *J. Am. Chem. Soc.,* 1989, 111, 8024 and International Patent Application WO 90/02749),). The loading capacity of the film is as high as that of a beaded matrix with the additional flexibility to accomodate multiple syntheses simultaneously. The PEPS film may be fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. Also, experiments with other geometries of the PEPS polymer such as, for example, non-woven felt, knitted net, sticks or microwell plates have not indicated any limitations of the synthetic efficacy.

Further support media amenable to the present invention include without limitation particles based upon copolymers of dimethylacrylamide cross-linked with N,N'-bisacryloylethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl safcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.,* 1975, 97, 6584, *Bioorg. Chem.* 1979, 8, 351, and J. C. S. Perkin 1538 (1981)).

Further support media amenable to the present invention include without limitation a composite of a resin and another material that is also substantially inert to the organic synthesis reaction conditions employed. One exemplary composite (see Scott, et al., *J. Chrom. Sci.,* 1971, 9, 577) utilizes glass particles coated with a hydrophobic, cross-linked styrene polymer containing reactive chloromethyl groups, and is supplied by Northgate Laboratories, Inc., of Hamden, Conn., USA. Another exemplary composite contains a core of fluorinated ethylene polymer onto which has been grafted polystyrene (see Kent and Merrifield, *Israel J. Chem.* 1978, 17, 243 and van Rietschoten in *Peptides* 1974, Y. Wolman, Ed., Wiley and Sons, New York, 1975, pp. 113–116). Contiguous solid supports other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345). Acrylic acid-grafted polyethylene-rods and 96-microtiter wells to immobilize the growing peptide chains and to perform the compartmentalized synthesis. (Geysen, et al., *Proc. Natl. Acad. Sci. USA,* 1984, 81, 3998). A "tea bag" containing traditionally-used polymer beads. (Houghten, *Proc. Natl. Acad. Sci. USA,* 1985, 82, 5131). Simultaneous use of two different supports with different densities (Tregear, *Chemistry and Biology of Peptides*, J. Meienhofer, ed., Ann Arbor Sci. Publ., Ann Arbor, 1972 pp. 175–178). Combining of reaction vessels via a manifold (Gorman, *Anal. Biochem.,* 1984, 136, 397). Multicolumn solid-phase synthesis (e.g., Krchnak, et al., *Int. J. Peptide Protein Res.,* 1989, 33, 209), and Holm and Meldal, in "Proceedings of the 20th European Peptide Symposium", G. Jung and E. Bayer, eds., Walter de Gruyter & Co., Berlin, 1989 pp. 208–210). Cellulose paper (Eichler, et al., *Collect. Czech. Chem. Commun.,* 1989, 54, 1746). Support mediated synthesis of peptides have also been reported (see, *Synthetic Peptides: A User's Guide*, Gregory A. Grant, Ed. Oxford University Press 1992; U.S. Pat. Nos. 4,415,732; 4,458,066; 4,500,707; 4,668,777; 4,973,679; 5,132,418; 4,725,677 and Re-34,069.)

Support bound oligonucleotide synthesis relies on sequential addition of nucleotides to one end of a growing chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725, 677 and Re. 34,069.

Commercially available equipment routinely used for the support media based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), *Oligonucleotides and Analogues*, a Practical Approach, Oxford University Press, New York (1991).

Another modification of oligomeric comounds is chemically linking one or more moieties or conjugates which enhance properties including activity, cellular distribution and cellular uptake. The conjugate groups can be covalently bound to functional groups such as primary or secondary hydroxyl groups. Conjugate groups of the invention include but are not limited to lipid moieties such as intercalators, reporter molecules, polyamides, polyethers, lipids, biotin, phenazine, folate, phenanthridine, anthraquinone, acridine, fluoresceins, rhodamines, coumarins, dyes, a cholesterol moiety (Letsinger et al., Proc. Natl. Acad. Sci. USA, 1989, 86, 6553–6556), cholic acid (Manoharan et al., Bioorg. Med. Chem. Let., 1994, 4, 1053–1060), a thioether, e.g., hexyl-S-tritylthiol (Manoharan et al., Ann. N.Y. Acad. Sci., 1992, 660, 306–309; Manoharan et al., Bioorg. Med. Chem. Let., 1993, 3, 2765–2770), a thiocholesterol (Oberhauser et al., Nucl. Acids Res., 1992, 20, 533–538), an aliphatic chain, e.g., dodecandiol or undecyl residues (Saison-Behmoaras et al., EMBO J., 1991, 10, 1111–1118; Kabanov et al., FEBS Lett., 1990, 259, 327–330; Svinarchuk et al., Biochimie, 1993, 75, 49–54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651–3654; Shea et al., Nucl. Acids Res., 1990, 18, 3777–3783), a polyamine or a polyethylene glycol chain (Manoharan et al., Nucleosides & Nucleotides, 1995, 14, 969–973), or adamantane acetic acid (Manoharan et al., *Tetrahedron Lett.*, 1995, 36, 3651–3654), a palmityl moiety (Mishra et al., Biochim. Biophys. Acta, 1995, 1264, 229–237), an octadecylamine or hexylamino-carbonyl-oxycholesterol moiety (Crooke et al., J. Pharmacol. Exp. Ther., 1996, 277, 923–937), groups that enhance the pharmacodynamic properties of oligomeric compounds, and groups that enhance the pharmacokinctic properties of oligomers. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Further representative ligand moieties are disclosed in International Patent Application PCT/US92/09196, filed Oct. 23, 1992 the entire disclosure of which is incorporated herein by reference.

Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indcmethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

One skilled in the art will recognize that other variations are possible within the general framework of the invention set forth herein. The present invention may be further appreciated upon reference to the following illustrative, non-limiting examples.

EXAMPLES

Example 1

Synthesis of T-T phosphate dimer: 100 milligram (4 micromole) of 5'-O-dimethoxytritylthymidine bonded to a support, CPG (controlled pore glass), through an ester linkage was taken in a glass reactor, and a dichloromethane solution of 3% dichloroacetic acid (volume/volume) was added to deprotect the 5'-hydroxyl group of the support-bound thymidine. The support was washed with dichloromethane and then with acetonitrile. Then, a 0.2 M solution of 5'-O-(4,4'-dimethoxytrityl)thymidine-3'-O-methyl-N,N-diisopropylphosphoramidite in acetonitrile and a 0.4 M solution of 1H-tetrazole in acetonitrile was added to the glass reactor, and allowed to react at room temperature for 5 minutes to produce a phosphite triester. The support was washed with acetonitrile, and then a 0.1 M solution of iodine in water/pyridine/THF (2:20:80) was added and allowed to react at room temperature for 2 minutes to produce a support-bound phosphate triester. The support was then washed with acetonitrile.

The support-bound phosphotriester T—T-dimer was treated with a solution of 2-methyl-5-tert-butylthiophenol:triethylamine:acetonitrile (1:1:3) for 2 hours to remove the methyl phosphorus protecting group from the phosphate, and then with 30% aqueous ammonium hydroxide solution for 90 minutes to cleave the dimer from the support. The resulting aqueous solution was filtered and concentrated under reduced pressure to give the T—T phosphate dimer.

Example 2

Synthesis of dC-T phosphate dimer: 100 milligram (4 micromole) of 5'-O-dimethoxytritylthymidine bonded to a support, CPG (controlled pore glass), through an ester linkage was taken in a glass reactor, and a dichloromethane solution of 3% dichloroacetic acid (volume/volume) was added to deprotect the 5'-hydroxyl group of the support-bound thymidine. The support was washed with dichloromethane and then with acetonitrile. Then, a 0.2 M solution of $N^4$-benzoyl-5'-O-(4,4'-dimethoxytrityl)-2'-deoxycytidine-3'-O-methyl-N,N-diisopropylphosphoramidite in acetonitrile and a 0.4 M solution of 1H-tetrazole in acetonitrile was added to the glass reactor and allowed to react at room temperature for 5 minutes to produce a support-bound dC-T phosphite triester. The support was washed with acetonitrile, and then a 0.1 M solution of iodine in water/pyridine/THF (2:20:80) was added and allowed to react at room temperature for 2 minutes to produce a support-bound dC-T phosphate triester. The support was then washed with acetonitrile.

The support-bound phosphotriester was treated with a solution of 2-methyl-5-tert-butylthiophenol: triethylamine:acetonitrile (1:1:3) for 2 hours to remove the methyl phosphorus protecting group, and then with 30% aqueous ammonium hydroxide solution for 90 minutes to cleave the dC-T phosphate dimer from the support. The aqueous solution was filtered and concentrated under reduced pressure to give the phosphate dimer of dC-T.

Example 3

Synthesis of 5'-TTTTTTT-3' phosphate heptamer: 50 milligram (2 micromole) of 5'-O-dimethoxytritylthymidine bonded to a support, CPG (controlled pore glass), through an ester linkage was taken in a glass reactor, and a dichloromethane solution of 3% dichloroacetic acid (volume/volume) was added to deprotect the 5'-hydroxyl group of the support-bound thymidine. The support-bound thymidine was washed with acetonitrile. Then, a 0.2 M solution of 5'-O-(4,4'-dimethoxytrityl)thymidine-3'-O-methyl-N,N-diisopropylphosphoramidite in acetonitrile and a 0.4 M solution of 1H-tetrazole in acetonitrile was added, and allowed to react at room temperature for 5 minutes to produce a support-bound T-T phosphite dimer. The support-bound phosphite dimer was washed with acetonitrile, and then a solution of acetic anhydride/lutidine/THF (1:1:8), and N-methylimidazole/THF was added to cap the unreacted 5'-hydroxyl group. Then a 0.1 M solution of iodine in water/pyridine/THF (2:20:80) was added and allowed to react at room temperature for 3 minutes to produce a support-bound T—T phosphate triester dimer. The support-bound dimer was washed with acetonitrile. This complete cycle (i.e. detritylation, phosphitylation and oxidation) was repeated five more times to produce the completely methyl phosphorus protected, support-bound thymidine heptamer.

The support-bound heptamer was first treated with a solution of 2-methyl-5-tert-butylthiophenol: triethylamine:acetonitrile (1:1:3) for 2 hours to remove the methyl phosphorus protective group, and then with 30% aqueous ammonium hydroxide solution for 90 minutes to cleave the heptamer from the support. The aqueous solution was filtered and concentrated under reduced pressure to give a phosphate heptamer of TTTTTTT.

Example 4

Synthesis of 5'-d(GACTT)-3' phosphate tetramer: 50 milligram (2 micromole) of 5-O-dimethoxytritylthymidine bonded to a support, CPG (controlled pore glass), through an ester linkage was taken in a glass reactor, and a dichloromethane solution of 3% dichloroacetic acid (volume/volume) was added to deprotect the 5'-hydroxyl group of the support-bound thymidine. The support was washed with acetonitrile. Then, a 0.2 M solution of 5'-O-(4,4-dimethoxytrityl)thymidine-3'-O-methyl-N,N-diisopropylphosphoramidite in acetonitrile and a 0.4 M solution of 1H-tetrazole in acetonitrile was added, and allowed to react at room temperature for 5 minutes to form a T—T phosphite dimer. The phosphite dimer was washed with acetonitrile, and then a solution of acetic anhydride/lutidine/THF (1:1:8), and N-methyl imidazole/THF was added to cap the unreacted 5'-hydroxyl group. Then a 0.1 M solution of iodine in water/pyridine/THF (2:20:80) was added and allowed to react at room temperature for 3 minutes to produce a support-bound T—T phosphate triester dimer. The support was then washed with acetonitrile.

A dichloromethane solution of 3% dichloroacetic acid (volume/volume) was added to deprotect the 5'-hydroxyl group of the 5'-terminal thymidine. The support was then washed with acetonitrile. Then, a 0.2 M solution of $N^4$-benzoyl-5'-O-(4,4'-dimethoxytrityl)-2'-deoxycytidine-3'-O-methyl-N,N-diisopropylphosphoramidite) in acetonitrile and a 0.4 M solution of 1H-tetrazole in acetonitrile was added to the reactor and allowed to react at room temperature for 5 minutes to form a phosphitylated, support-bound product. The support was washed with acetonitrile, and then a solution of acetic anhydride/lutidine/THF (1:1:8), and N-methyl imidazole/THF was added to cap the unreacted 5'-hydroxyl group. Then a 0.1 M solution of iodine in water/pyridine/THF (2:20:80) was added and allowed to react at room temperature for 3 minutes to oxidize the phosphite to a phosphate. The support was then washed with acetonitrile.

A dichloromethane solution of 3% dichloroacetic acid (volume/volume) was added to deprotect the 5'-hydroxyl group of the 5'-terminal cytotidine. The support was then washed with acetonitrile. Then, a 0.2 M solution of $N^6$-benzoyl-5'-O-(4,4'-dimethoxytrityl)-2'-deoxyadenosine-3'-O-methyl-N,N-diisopropylphosphoramidite) in anhydrous acetonitrile and a 0.4 M solution of 1H-tetrazole in acetonitrile was added, and allowed to react at room temperature for 5 minutes to form a phosphitylated, support-bound product. The support was then washed with acetonitrile, and then a solution of acetic anhydride/lutidine/THF (1:1:8), and N-methylimidazole/THF was added to cap the unreacted 5'-hydroxyl group. Then a 0.1 M solution of iodine in water/pyridine/THF (2:20:80) was added and allowed to react at room temperature for 3 minutes to oxidize the phosphite to a phosphate. The support was then washed with acetonitrile.

A dichloromethane solution of 3% dichloroacetic acid (volume/volume) was added to deprotect the 5'-hydroxyl group of the tetramer. The support was then washed with acetonitrile. Then, a 0.2 M solution of $N^2$-isobutyryl-5'-O-(4,4'-dimethoxytrityl)-2'-deoxyguanosine-3'-O-methyl-N,N-diisopropylphos-phoramidite in acetonitrile and a 0.4 M solution of 1H-tetrazole in acetonitrile was added, and allowed to react at room temperature for 5 minutes to form a support-bound phosphitylated product. The support was then washed with acetonitrile, and then a solution of acetic anhydride/lutidine/THF (1:1:8), and N-methylimidazole/THF was added to cap the unreacted 5'-hydroxyl group. Then a 0.1 M solution of iodine in water/pyridine/THF (2:20:80) was added and allowed to react at room temperature for 3 minutes to oxidize the phosphite to a phosphate. The support was then washed with acetonitrile.

The support-bound pentamer was first treated with a solution of 2-methyl-5-tert-butylthiophenol: triethylamine:acetonitrile (1:1:3) for 2 hours to remove the methyl phosphorus protecting groups, and then with 30% aqueous ammonium hydroxide solution for 90 minutes at room temperature and then incubated at 55° C. for 16 hour to remove the pentamer from the solid support. The resulting aqueous solution was filtered and concentrated under reduced pressure to give a phosphate tetramer of 5'-d (GACTT)-3'.

Example 5

Synthesis of 5'-d(TCC-CGC-CTG-TGA-CAT-GCA-TT)-3' phosphate 20-mer (SEQ ID NO. 1): The synthesis of this sequence was performed on a Pharmacia OligoPilot II Synthesizer on a 120 micromole scale using p-methoxy phosphoramidites and Pharmacia's Primer HL30™ solid support. Detritylation was performed using 3% dichloroacetic acid in toluene(volume/volume). Oxidation was performed using a 0.1 M solution of iodine in water/pyridine/THF (2:20:80) for 3 minutes. At the end of synthesis, the support-bound oligonucleotide was treated first with a solution of 2-methyl-5-tert-butylthiophenol:triethylamine:acetonitrile (1:1:3) for 2 hours to remove the methyl phosphorus protecting groups, and then with 30% aqueous ammonium hydroxide solution for 90 minutes at room temperature and then incubated at 55° C. for 16 hour to remove the oligonucleotide from the solid support. The oligonucleotide was purified in the usual manner.

Example 6

Synthesis of 5'-d(GCC-CAA-GCT-GGC-ATC-CGT-CA)-3' phosphate 20-mer (SEQ ID NO. 2): The synthesis of this sequence was performed on a Pharmacia OligoPilot II Synthesizer on a 320 micromole scale using the p-methoxy phosphoramidites and Pharmacia's Primer HL30™ solid support. Detritylation was performed using 3% dichloroacetic acid in toluene (volume/volume). Oxidation was performed using a 0.1 M solution of iodine in water/pyridine/THF (2:20:80) for 3 minutes. At the end of synthesis, the support-bound oligonucleotide was treated first with a solution of 2-methyl-5-tert-butylthiophenol:triethylamine:acetonitrile (1:1:3) for 2 hours to remove the methyl phosphorus protecting groups, and then with 30% aqueous ammonium hydroxide solution for 90 minutes at room temperature and then incubated at 55° C. for 16 hour to cleave the 20-mer from the solid support. The oligonucleotide was purified in the usual manner.

Example 7

Synthesis of 5'-d(GCG-TTT-GCT-CTT-CTT-CTT-GCG)-3' phosphate 21-mer (SEQ ID NO. 3): The synthesis of this sequence was performed on a Pharmacia OligoPilot II Synthesizer on a 220 micromole scale using the p-methoxy phosphoramidites and Pharmacia's Primer HL30™ solid support. Detritylation was performed using 3% dichloroacetic acid in toluene (volume/volume). Oxidation was performed using a 0.1 M solution of iodine in water/pyridine/THF (2:20:80) for 3 minutes. At the end of synthesis, the support-bound oligonucleotide was treated first with a solution of 2-methyl-5-tert-butylthiophenol:triethylamine:acetonitrile (1:1:3) for 2 hours to remove the phosphorus methyl protecting groups and then with 30% aqueous ammonium hydroxide solution for 90 minutes at room temperature and then incubated at 55° C. for 16 hour to remove the 21-mer from the solid support. The oligonucleotide was purified in the usual manner.

Example 8

Synthesis of 5'-d(GTT-CTC-GCT-GGT-GAG-TTT-CA)-3' phosphate 20-mer (SEQ ID NO. 4): The synthesis of this sequence was performed on a Pharmacia OligoPilot II Synthesizer on a 220 micromole scale using the p-methoxy phosphoramidites and Pharmacia's Primer HL30™ solid support. Detritylation was performed using 3% dichloroacetic acid in toluene (volume/volume). Oxidation was performed using a 0.1 M solution of iodine in water/pyridine/THF (2:20:80) for 3 minutes. At the end of synthesis, the support-bound oligonucleotide was treated first with a solution of 2-methyl-5-tert-butylthiophenol:triethylamine:acetonitrile (1:1:3) for 2 hours to remove the phosphorus methyl protecting groups and then with 30% aqueous ammonium hydroxide solution for 90 minutes at room temperature and then incubated at 55° C. for 16 hour to cleave the 20-mer from the solid support. The oligonucleotide was purified in the usual manner.

Example 9

Synthesis of T—T phosphorothioate dimer: 100 Milligram (4 micromole) of 5'-O-dimethoxytritylthymidine bonded to a support, CPG (controlled pore glass), through an ester linkage was taken in a glass reactor, and a dichloromethane solution of 3% dichloroacetic acid (volume/volume) was added to deprotect the 5'-hydroxyl group of the support-bound thymidine. The support was then washed with dichloromethane and then with acetonitrile. Then, a 0.2 M solution of 5'-O-(4,4'-dimethoxytrityl)thymidine-3'-O-methyl-N,N-diisopropylphosphoramidite in acetonitrile and a 0.4 M solution of 1H-tetrazole in acetonitrile was added, and allowed to react at room temperature for 5 minutes to form a phosphite triester product on the solid support. The support was then washed with acetonitrile, and then a 0.2 M solution of phenylacetyl disulfide (PADS) in 3-picoline:acetonitrile (1:1) was added and allowed to react at room temperature for 2 minutes to produce the phosphorothioate triester. The support was washed with acetonitrile and then a solution of acetic anhydride/lutidine/THF (1:1:8), and N-methyl imidazole/THF was added to cap the unreacted 5'-hydroxyl group. The support was then washed with acetonitrile.

The support was first treated with a solution of 2-methyl-5-tert-butylthiophenol: triethylamine:acetonitrile (1:1:3) for 2 hours to remove the phosphorus methyl protecting group and then with 30% aqueous ammonium hydroxide solution for 90 minutes to cleave the dimer from the solid support. The resulting aqueous solution was filtered and concentrated under reduced pressure to give phosphorothioate dimer of T—T.

Example 10

Synthesis of C-T phosphorothioate dimer: 100 Milligram (4 micromole) of 5'-O-dimethoxytritylthymidine bonded to a support, CPG (controlled pore glass), through an ester linkage was taken in a glass reactor, and a dichloromethane solution of 3% dichloroacetic acid (volume/volume) was added to deprotect the thymidyl 5'-hydroxyl group. The support was then washed with acetonitrile. Then, a 0.2 M solution of $N^4$-benzoyl-5'-O-(4,4'-dimethoxytrityl)-2'-deoxycytidine-3'-O-methyl-N,N-diisopropylphosphoramidite in acetonitrile and a 0.4 M solution of 1H-tetrazole in acetonitrile was added, and allowed to react at room temperature for 5 minutes to form a phosphitylated product. The support was washed with acetonitrile, and then a 0.2 M solution of phenylacetyl disulfide in 3-picoline:acetonitrile (1:1) was added and allowed to react at room temperature for 2 minutes to form the phosphorothioate triester. The support was washed with acetonitrile and then a solution of acetic anhydride/lutidine/THF (1:1:8), and N-methyl imidazole/THF was added to cap the unreacted 5'-hydroxyl group. The support was then washed with acetonitrile.

The support-bound phosphorothioate triester was first treated with a solution of 2-methyl-5-tertbutylthiophenol:triethylamine:acetonitrile (1:1:3) for 2 hours to remove the phosphorus methyl protecting group and then with 30% aqueous ammonium hydroxide solution for 90 minutes to cleave the dC-T phosphorothioate dimer product from the solid support. The aqueous solution was filtered and concentrated under reduced pressure to give a phosphorothioate dimer of dC-T.

Example 11

Synthesis of fully-modified 5'-TTTTTTT-3' phosphorothioate heptamer: 50 Milligram (2 micromole) of 5'-O-dimethoxytritylthymidine bound to a solid support, CPG (controlled pore glass), through an ester linkage was taken up in a glass reactor, and a toluene solution of 3% dichloroacetic acid (volume/volume) was added to deprotect the 5-hydroxyl group of the support-bound thymidine. The support was washed with acetonitrile. Then, a 0.2 M solution of 5'-O-(4,4'-dimethoxytrityl)thymidine-3'-O-methyl N,N-diisopropylphosphoramidite in acetonitrile and a 0.4 M solution of 1H-tetrazole in acetonitrile was added and allowed to react at room temperature for 5 minutes to form a phosphitylated product. The support was washed with acetonitrile, and then a 0.2 M solution of phenylacetyl disulfide in 3-picoline:acetonitrile (1:1) was added and allowed to react at room temperature for 2 minutes to form a support-bound phosphorothioate triester. The support was washed with acetonitrile and then a solution of acetic anhydride/lutidine/THF (1:1:8), and N-methylimidazole/THF was added to cap the unreacted 5'-hydroxyl group. The support was then washed with acetonitrile.

This complete cycle was repeated five more times to produce the completely phosphorus methyl protected thymidine heptamer, which was treated first with a solution of 2-methyl-5-tert-butylthiophenol: triethylamine:acetonitrile (1:1:3) for 2 hours to remove the phosphorus methyl protecting groups and then with 30% aqueous ammonium hydroxide solution for 90 minutes at room temperature to cleave the hepatmer from the solid support. The aqueous solution was filtered, and concentrated under reduced pressure to give a phosphorothioate heptamer, TTTTTTT.

Example 12

Synthesis of 5'-d(GACT)-3' phosphorothioate tetramer: 50 Milligram (2 micromole) of 5'-O-dimethoxytritylthymidine bound to a solid support, CPG (controlled pore glass), through an ester linkage was taken up in a glass reactor, and a toluene solution of 3% dichloroacetic acid in toluene (volume/volume) was added to deprotect the 5'-hydroxyl group. The support was washed with acetonitrile. Then, a 0.2 M solution of 5'-O-(4,4'-dimethoxytrityl)thymidine-3'-O-methyl N,N-diisopropylphosphoramidite in acetonitrile and a 0.4 M solution of 1H-tetrazole in acetonitrile was added, and allowed to react at room temperature for 5 minutes to form the dC-T phosphite triester. The support was washed with acetonitrile, and then a 0.2 M solution of phenylacetyl disulfide in acetonitrile:3-picoline (1:1 v/v) was added and allowed to react at room temperature for 3 minutes to form the dC-T thiophosphate triester. The support was washed with acetonitrile and then a solution of acetic anhydride/lutidine/THF (1:1:8), and N-methyl imidazole/THF was added to cap the unreacted 5'-hydroxyl group. The support was washed with acetonitrile.

A solution of 3% dichloroacetic acid in toluene (volume/volume) was added to deprotect the 5'-hydroxyl group of the 5-terminal dC. The support was washed with acetonitrile.

Then, a 0.2 M solution of $N^4$-benzoyl-5'-O-(4,4'-dimethoxytrityl)-2'-deoxycytidine-3'-O-methyl N,N-diisopropylphosphoramidite in acetonitrile and 0.4 M solution of 1H-tetrazole in acetonitrile was added, and allowed to react at room temperature for 5 minutes to form the phosphitylated product. The support was washed with acetonitrile, and then a 0.2 M solution of phenylacetyl disulfide in acetonitrile:3-picoline (1:1 v/v) was added and allowed to react at room temperature for 3 minutes to oxidize the phosphite to a thiophosphate. The support was washed with acetonitrile and then a solution of acetic anhydride/lutidine/THF (1:1:8), and N-methyl imidazole/THF was added to cap any unreacted 5'-hydroxyl group. The support was washed with acetonitrile.

A solution of 3% dichloroacetic acid in toluene (volume/volume) was added to deprotect the 5'-hydroxyl group of the 5'-terminal cytidine. The support was washed with acetonitrile. Then, a 0.2 M solution of $N^6$-benzoyl-5'-O-(4,4'-dimethoxytrityl)-2'-deoxyadenosine-3'-O-methyl N,N-diisopropylphosphoramidite in anhydrous acetonitrile and a 0.4 M solution of 1H-tetrazole in acetonitrile was added, and allowed to react at room temperature for 5 minutes. The support was washed with acetonitrile, and then a 0.2 M solution of phenylacetyl disulfide in acetonitrile:3-picoline (1:1 v/v) was added and allowed to react at room temperature for 3 minutes to oxidize the phosphite to a thiophosphate. The support was washed with acetonitrile and then a solution of acetic anhydride/lutidine/THF (1:1:8), and N-methylimidazole/THF was added to cap the unreacted 5'-hydroxyl group. The support was washed with acetonitrile.

A solution of 3% dichloroacetic acid in toluene (volume/volume) was added to deprotect the 5'-hydroxyl group of the 5'-terminal adenosine. The support was washed with acetonitrile. Then, a 0.2 M solution of $N^2$-isobutyryl-5'-O-(4,4'-dimethoxytrityl)-2'-deoxyguanosine-3'-O-methyl N,N-diisopropylphosphoramidite in acetonitrile and a 0.4 M solution of 1H-tetrazole in acetonitrile was added, and allowed to react at room temperature for 5 minutes to form a phosphitylated product. The support was washed with acetonitrile, and then a 0.2 M solution of phenylacetyl disulfide in acetonitrile:3-picoline (1:1 v/v) was added and allowed to react at room temperature for 3 minutes to oxidize the phosphite to a thiophosphate. The support was washed with acetonitrile and then a solution of acetic anhydride/lutidine/THF (1:1:8), and N-methyl imidazole/THF was added to cap any unreacted 5'-hydroxyl group. The product was washed with acetonitrile.

The support was then treated with a solution of 2-methyl-5-tert-butylthiophenol:triethylamine:acetonitrile (1:1:3) for 2 hours to remove the phosphorus methyl protecting groups, and then with 30% aqueous ammonium hydroxide solution for 90 minutes at room temperature and then incubated at 55° C. for 24 hour to cleave the tetramer from the support. The aqueous solution was filtered and concentrated under reduced pressure and purified to give a phosphorothioate tetramer of 5'-dG-dA-dC-T-3'.

Example 13

Synthesis of fully-modified 5'-d(TCC-CGC-CTG-TGA-CAT-GCA-TT)-3' phosphorothioate 20-mer (SEQ ID NO. 5): The synthesis of this sequence was performed on a Pharmacia OligoPilot II Synthesizer on a 180 micromole scale using p-methoxy phosphoramidites and Pharmacia's Primer HL30™ solid support. Detritylation was performed using 3% dichloroacetic acid in toluene (volume/volume).

Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support containing the compound was treated first with a solution of 2-methyl-5-tert-butylthiophenol:triethylamine:acetonitrile (1:1:3) for 2 hours to remove the phosphorus methyl protecting groups, and then with 30% aqueous ammonium hydroxide solution for 90 minutes at room temperature and then incubated at 55° C. for 24 hour to cleave the 20-mer from the solid support. The aqueous solution was filtered and concentrated under reduced pressure and purified to give the desired 20-mer product.

Example 14

Synthesis of fully-modified 5'-d(GCC-CAA-GCT-GGC-ATC-CGT-CA)-3' phosphorothioate 20-mer (SEQ ID NO. 6): The synthesis of this sequence was performed on a Pharmacia OligoPilot II Synthesizer on a 190 micromole scale using the p-methoxy phosphoramidites and Pharmacia's Primer HL30™ solid support. Detritylation was performed using 3% dichloroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was treated first with a solution of 2-methyl-5-tert-butylthiophenol:triethylamine:acetonitrile (1:1:3) for 2 hours to remove the phosphorus methyl protecting groups, and then with 30% aqueous ammonium hydroxide solution for 90 minutes at room temperature and then incubated at 55° C. for 24 hour to cleave the 20-mer from the solid support. The aqueous solution was filtered and concentrated under reduced pressure and purified to give the desired 20-mer product.

Example 15

Synthesis of fully-modified 5'-d(TCC-CGC-CTG-TGA-CAT-GCA-TT)-3' phosphorothioate 20-mer (SEQ ID NO. 5): The synthesis this sequence was performed on a Pharmacia OligoPilot II Synthesizer on a 160 micromole scale using the p-methoxy phosphoramidites and Pharmacia's Primer HL30™ solid support. Detritylation was performed using 3% dichloroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support containing the compound was treated first with a solution of 2-methyl-5-tert-butylthiophenol:triethylamine:acetonitrile (1:1:3) for 2 hours to remove the phosphorus methyl protecting groups, and then with 30% aqueous ammonium hydroxide solution for 90 minutes at room temperature, and then incubated at 55° C. for 24 hour to cleave the 20-mer from the support. The aqueous solution was filtered and concentrated under reduced pressure and purified to give the desired 20-mer product.

Example 16

Synthesis of fully-modified 5'-d(TCC-CGC-CTG-TGA)-2'-methoxyethyl-(CAT-GCA-TT)-3' phosphorothioate 20-mer (SEQ ID NO. 7): The synthesis of this sequence was performed on a Pharmacia OligoPilot II Synthesizer on a 160 micromole scale using the p-methoxy phosphoramidites and Pharmacia's Primer HL30™ solid support. Detritylation was performed using 3% dichloroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support containing the compound was treated first with a solution of 2-methyl-5-tert-butylthiophenol:triethylamine:acetonitrile (1:1:3) for 2 hours to remove the phosphorus methyl protecting groups, and then with 30% aqueous ammonium hydroxide solution for 90 minutes at room temperature, and then incubated at 55° C. for 24 hour. The aqueous solution was filtered and concentrated under reduced pressure and purified to give the desired 20-mer product.

Example 17

Synthesis of fully-modified 5'-(2'-methoxyethyl)-(CAGC)-d(AGC-AGA-GTC-TTTCA)-2'-methoxyethyl-(TCAT)-3' phosphorothioate 20-mer (SEQ ID NO. 8): The synthesis of this sequence was performed on a Pharmacia OligoPilot II Synthesizer on a 160 micromole scale using the p-methoxy phosphoramidites and Pharmacia's Primer HL30™ solid support. Detritylation was performed using 3% dichloroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support containing the compound was treated first with a solution of 2-methyl-5-tert-butylthiophenol:triethylamine:acetonitrile (1:1:3) for 2 hours to remove the phosphorus methyl protecting groups, and then with 30% aqueous ammonium hydroxide solution for 90 minutes at room temperature, and then incubated at 55° C. for 24 hour to cleave the 20-mer from the solid support. The aqueous solution was filtered and concentrated under reduced pressure and purified to give the desired 20-mer product.

Example 18

Synthesis of fully-modified 5'-(2'-methoxyethyl)-(TCC-CGC)-d(CTG-TGA-CA)-2'-methoxyethyl-(TGC-ATT)-3' phosphorothioate 20-mer (SEQ ID NO. 9): The synthesis of this sequence was performed on a Pharmacia OligoPilot II Synthesizer on a 210 micromole scale using the p-methoxy phosphoramidites and Pharmacia's Primer HL30™ solid support. Detritylation was performed using 3% dichloroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support containing the compound was treated first with a solution of 2-methyl-5-tert-butylthiophenol:triethylamine:acetonitrile (1:1:3) for 2 hours to remove the phosphorus methyl protecting groups, and then with 30% aqueous ammonium hydroxide solution for 90 minutes at room temperature, and then incubated at 55° C. for 24 hour to cleave the 20-mer from the solid support. The aqueous solution was filtered and concentrated under reduced pressure and purified to give the desired 20-mer product.

Example 19

Synthesis of fully-modified 5'-(2'-methoxyethyl)-(GCT-GA)-d(TTA-GAG-AGA-G)-2'-methoxyethyl-(GTC-CC)-3' phosphorothioate 20-mer (SEQ ID NO. 10): The synthesis of this sequence was performed on a Pharmacia OligoPilot II Synthesizer on a 160 micromole scale using the p-methoxy phosphoramidites and Pharmacia's Primer HL30™ solid support. Detritylation was performed using 3% dichloroacetic acid in toluene (volume/volume). Activation of phosphoramidites was done with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support containing the compound was treated first with a solution of 2-methyl-5-tert-butylthiophenol:triethylamine:acetonitrile (1:1:3) for 2 hours to remove the phosphorus methyl protecting groups, and then with 30% aqueous ammonium hydroxide solution for 90 minutes at room temperature, and then incubated at 55° C. for 24 hour to cleave the 20-mer from the solid support. The aqueous solution was filtered and concentrated under reduced pressure and purified to give the desired 20-mer product.

As can be seen in the foregoing examples, the present invention provides reagents and methods suitable for removing phosphorus protecting groups, and in particular alkyl phosphorus protecting groups, from a synthetically prepared, phosphorus-protected oligonucleotide. The methods and reagents of the present invention provide a convenient, non-malodorous, industrially scalable means to deprotect phosphorus-protected oligonucleotides. The method avoids production of acrylonitrile adducts that characterize the Köster amidite method. Other characteristics and advantages of the present invention will become apparent to the skilled person upon consideration of the following claims.

The person having skill in the art will recognize that further embodiments are possible within the general scope of the foregoing description and the attached claims, and it would be within the skill of such skilled person to practice the invention as generally described herein.

All references cited herein are expressly incorporated herein by reference.

What is claimed is:

1. A method of using a phosphorus-deprotecting compounds, wherein the compound is 2-methyl-5-t-butylthiophenol;

the method comprising contacting said phosphorus-deprotecting compound and a protected phosphorus-containing compound of formula II:

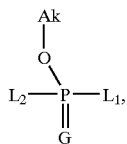

wherein Ak is $C_1$–$C_{10}$ alkyl, G is O or S, and $L_1$ and $L_2$ include one or more of: nucleotides linked by phosphate or thiophosphate groups, or oligonucleotide chains, for a period sufficient to remove Ak from the phosphorus-containing compound, thereby forming a deprotected compound of the formula:

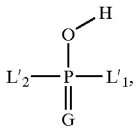

wherein G, has the same meaning as in formula II, $L'_1$ is $L_1$ optionally having at least one deprotected phosphorus group, and $L'_2$ is $L_2$ optionally having at least one deprotected phosphorus group.

2. The method of claim 1, wherein $L_1$ is of the formula:

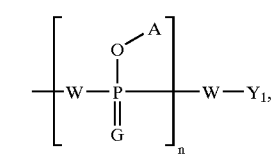

wherein each W is a monomeric nucleoside,
each A is H or a phosphorus protecting group,
n is 0 or a positive integer,
each G is 0 or S, and $Y_1$ is H, a protecting group, or a linking group to a solid support.

3. The process of claim 2, wherein each W is of the formula:

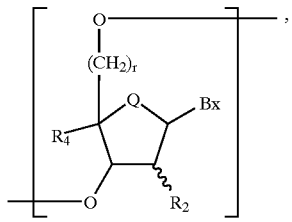

wherein Q is O, $B_x$ is a nucleobase, $R_2$ is H, OH, protected OH, SH, alkyl, alkenyi, alkynyl, aryl, alkoxy, alkenyloxy, alkynyloxy, aminoalkoxy, alkoxyalkoxy, alkylaminoalkoxy, imidazolylalkoxy, alkenylthio, alkynylthio, alkenylamino, alkynylamino, aryloxy, arylthio, aralkyloxy, aralkylthio, aralkylamino, N-phthalimido, halogen, carboxyl, nitro, nitroso, cyano, trifluoromethyl, trifluoromethoxy, imidazolyl, azido, hydrazino, aminooxy, isocyanato, isothiocyanato, sulfoxide, sulfone, disulfide, silyl, a heterocycle, a carbocycle, a polyamine, a polyamide, a polyalkylene glycol, or a polyether of the formula (O-alkyl)$_m$, where m is 1 to about 10, and $R_4$ is H, or $R_2$ and $R_4$ together form 2'-O—(CH$_2$)$_q$-4' or 2'-(CH$_2$)$_q$-4', wherein q is 1 or 2, or $R_2$ and $R_4$ together form 2'-CH$_2$—O—CH$_2$-4'; and r is 0 or 1.

4. The method of claim 3, wherein Q is O and r is 1.

5. The method of claim 1, wherein $L_2$ is of the formula:

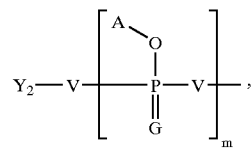

wherein each V is a monomeric nucleoside, m is 0 or a positive integer, each A is H or a phosphorus protecting group, each G is O or S, and $Y_2$ is H, a protecting group, or a linking group to a solid support.

6. The process of claim 5, wherein each V has the formula:

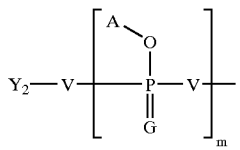

wherein Q is O, $B_x$ is a nucleobase, $R_2$ is H, OH, SH, alkyl, alkenyl, alkynyl, aryl, alkoxy, alkenyloxy, alkynyloxy, aminoalkoxy, alkoxyalkoxy, alkylaminoalkoxy, imidazolylalkoxy, alkenylthio, alkynylthio, alkenylamino, alkynylamino, aryloxy, arylthio, aralkyloxy, aralkylthio, aralkylamino, N-phthalimido, halogen, carboxyl, nitro, nitroso, cyano, trifluoromethyl, trifluoromethoxy, imidazolyl, azido, hydrazino, aminooxy, isocyanato, isothiocyanato, sulfoxide, sulfone, disulfide, silyl, a heterocycle, a carbocycle, a polyamine, a polyamide, a polyalkylene glycol, or a polyether of the formula (O-alkyl)$_m$, where in is 1 to about 10, and $R_4$ is H, or $R_2$ and $R_4$ together form 2'-O—(CH$_2$)$_q$-4' or 2'-(CH$_2$)$_q$-4', wherein q is 1 or 2, or $R_2$ and $R_4$ together form 2'-CH$_2$—O—CH$_2$-4'; and t is 0 or 1.

7. The method of claim 1, wherein $L_1$ is of the formula:

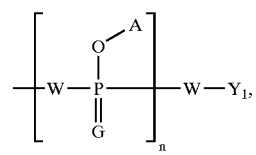

and $L_2$ is of the formula:

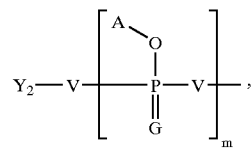

wherein each W is a monomeric nucleoside moiety each V is a monomeric nucleoside moiety n is 0 or a positive integer, m is 0 or a positive integer, each G is O or S, each A is H or a phosphorus protecting group, $Y_1$ is H, a protecting group or a linking group, wherein said linking group is conjugated to a solid support, and $Y_2$ is H, a protecting group or a linking group, wherein said linking group is conjugated to a solid support, with the proviso that $Y_1$ and $Y_2$ may not simultaneously be a linking group to a solid support.

8. The process of claim 7, wherein:

each W is a monomeric nucleoside of the formula:

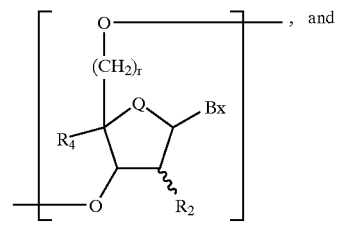

each V is a monomeric nucleoside of the formula:

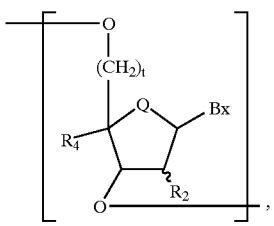

wherein each r and each t is independently 0 or 1, each Q is O, $B_x$ is a nucleobase, $R_2$ is H, OH, protected OH, SH, alkyl, alkenyl, alkynyl, aryl, alkoxy, alkenyloxy, alkynyloxy, aminoalkoxy, alkoxyalkoxy, alkylaminoalkoxy, imidazolylalkoxy, alkenylthio, alkynylthio, alkenylamino, alkynylamino, aryloxy, arylthio, aralkyloxy, aralkylthio, aralkylamino, N-phthalimido, halogen, carboxyl, nitro, nitroso, cyano, trifluoromethyl, trifluoromethoxy, imidazolyl, azido, hydrazino, aminooxy, isocyanato, isothiocyanato, sulfoxide, sulfone, disulfide, silyl, a heterocycle, a carbocycle, a polyamine, a polyamide, a polyalkylene glycol, or a polyether of the formula (O-alkyl)$_m$, where m is 1 to about 10, and $R_4$ is H, or $R_2$ and $R_4$ together form 2'-O—(CH$_2$)$_q$-4' or 2'-(CH$_2$)$_q$-4', wherein q is 1 or 2, or $R_2$ and $R_4$ together form 2'-CH$_2$—O—CH$_2$-4';

each r is 0 or 1; and each t is 0 or 1.

9. The process of claim 8, wherein each Q is O, each r is 1, each t is 1, and each $R_2$ is H, OH, protected OH, OCH$_3$, or OCH$_2$CH$_2$OCH$_3$.

10. The process of claim 9, wherein the sum of m and n is 0 to 60.

11. The process of claim 10, wherein the sum of m and n is 4 to 30.

12. The process of claim 11, wherein the sum of m and n is 4 to 20.

13. The process of claim 1, wherein L'$_1$ has the formula:

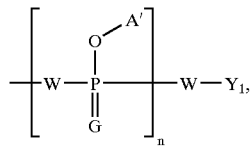

wherein each W is a monomeric nucleoside, each A' is H or a phosphorus protecting group, n is 0 or a positive integer, each G is O or S, and $Y_1$ is H, a protecting group, or a linking group to a solid support; and L'$_2$ has the formula:

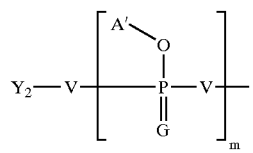

wherein each V is a monomeric nucleoside, in is 0 or a positive integer, each A' is H or a phosphorus protecting group, each G is O or S, $Y_2$ is H, a protecting group, or a linking group to a solid support, except that $Y_1$ and $Y_2$ cannot both be linking groups to a solid support.

14. The process of claim 13, wherein the sum of n and m is 0 to 60.

15. The process of claim 14, wherein, when the sum of n and m is 2 or greater, at least about 50% of the moieties A' are H.

16. The process of claim 13, wherein n is 0 or 1 and m is 0 or 1 and the sum of n and m is 0 or 1.

17. The process of claim 16, wherein each A' is H.

18. The process of claim 13, wherein the sum of n and m is 4 to 30.

19. The process of claim 18, wherein at least about 75% of the moieties A' are H.

20. The process of claim 13, wherein the sum of n and m is 10 to 30.

21. The process of claim 20, wherein at least about 90% of the moieties A' are H.

22. The process according to claim 13, wherein $Y_1$ is a 4,4'-dimethoxytriphenylmethyl (DMT) group.

23. The process according to claim 13, wherein $Y_2$ is H or is conjugated to a solid support.

24. The process according to claim 13, wherein each W is:

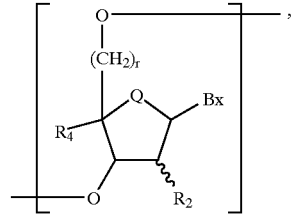

wherein Q is O, $B_x$ is a nucleobase, $R_2$ is H, OH, protected OH, SH, alkyl, alkenyl, alkynyl, aryl, alkoxy, alkenyloxy, alkynyloxy, aminoalkoxy, alkoxyalkoxy, alkylaminoalkoxy, imidazolylalkoxy, alkenylthio, alkynylthio, alkenylamino, alkynylamino, aryloxy, arylthio, aralkyloxy, aralkylthio, aralkylamino, N-phthalimido, halogen, carboxyl, nitro, nitroso, cyano, trifluoromethyl, trifluoromethoxy, imidazolyl, azido, hydrazino, aminooxy, isocyanato, isothiocyanato, sulfoxide, sulfone, disulfide, silyl, a heterocycle, a carbocycle, a polyamine, a polyamide, a polyalkylene glycol, or a polyether of the formula (O-alkyl)$_m$, where m is 1 to about 10, and $R_4$ is H, or $R_2$ and $R_4$ together form 2'-O—(CH$_2$)$_q$-4' or 2'-(CH$_2$)$_q$-4', wherein q is 1 or 2, or $R_2$ and $R_4$ together form 2'-CH$_2$—O—CH$_2$-4'; and r is 0 or 1, and each V is:

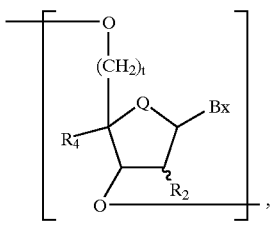

wherein Q is O,
B$_x$ is a nucleobase,
R$_2$ is H, OH, protected OH, SH, alkyl, alkenyl, alkynyl, aryl, alkoxy, alkenyloxy, alkynyloxy, aminoalkoxy, alkoxyalkoxy, alkylaminoalkoxy, imidazolylalkoxy, alkenylthio, alkynylthio, alkenylamino, alkynylamino, aryloxy, arylthio, aralkyloxy, aralkylthio, aralkylamino, N-phthalimido, halogen, nitro, nitroso, cyano, trifluoromethyl, trifluoromethoxy, imidazolyl, azido, hydrazino, aminooxy, isocyanato, isothiocyanato, sulfoxide, sulfone, disulfide, silyl, a heterocycle, a carbocycle, a polyamine, a polyamide, a polyalkylene glycol, or a polyether of the formula (O-alkyl)$_m$, where m is 1 to about 10,
and R$_4$ is H,
or R$_2$ and R$_4$ together form 2'-O—(CH$_2$)$_q$-4' or 2'-(CH$_2$)$_q$-4', wherein q is 1 or 2, or R$_2$ and R$_4$ together form 2'-CH$_2$—O—CH$_2$-4'; and
t is 0 or 1.

25. The process of claim 24, wherein each Q is O, each r is 1, each r is 1, and each R$_2$ is independently H, OH, OCH$_3$ or OCH$_2$CH$_2$OCH$_3$.

26. A process of making a compound of the formula:

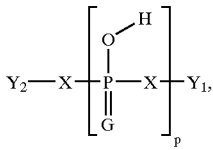

wherein each X is independently a nucleoside monomer,
G is O or S,
Y$_1$ is H, a protecting group or a linking group conjugated to a solid support;
Y$_2$ is H, a protecting group or a linking group conjugated to a solid support, except that Y$_1$ and Y$_2$ cannot be simultaneously a linking group conjugated to a solid support;
p is a positive integer;
the process comprising contacting a phosphorus-protected compound of the formula:

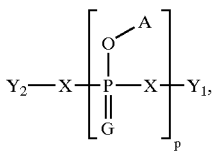

wherein A is a phosphorus protecting group,
with a phosphorus-deprotection non-malodorous thiol compound selected from 2-methyl-5-t-butylthiophenol for a time sufficient to remove said phosphorus protecting group.

27. The process according to claim 26, wherein each X independently has the formula:

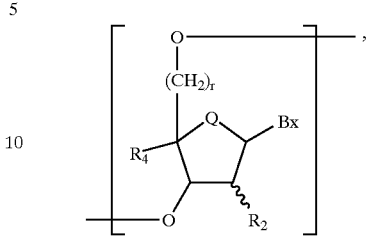

wherein each B$_x$ is a nucleobase;
each r is independently 0 or 1;
each Q is independently O;
R$_2$ is H, OH, SH, alkyl, alkenyl, alkynyl, aryl, alkoxy, alkenyloxy, alkynyloxy, aminoalkoxy, alkoxyalkoxy, alkylaminoalkoxy, imidazolylalkoxy, alkenylthio, alkynylthio, alkenylamino, alkynylamino, aryloxy, arylthio, aralkyloxy, aralkylthio, aralkylamino, N-phthalimido, halogen, carboxyl, nitro, nitroso, cyano, trifluoromethyl, trifluoromethoxy, imidazolyl, azido, hydrazino, aminooxy, isocyanato, isothiocyanato, sulfoxide, sulfone, disulfide, silyl, a heterocycle, a carbocycle, a polyamine, a polyamide, a polyalkylene glycol, or a polyether of the formula (O-alkyl)$_m$, where m is 1 to about 10,
and R$_4$ is H, or R$_2$ and R$_4$ together from —(CH$_2$)$_q$—, wherein q is 1 or 2.

28. The process of claim 27, wherein each Q is O and each r is 1.

29. The process of claim 27, wherein each R$_2$ is independently H, OH, protected OH, protected OH, OCH$_3$ or OCH$_2$CH$_2$OCH$_3$.

30. The process of claim 27, wherein each A is independently C$_1$–C$_{10}$ alkyl.

31. The process of claim 20, wherein each A is methyl.

32. The process of claim 26, wherein p is an integer in the range of 1 to 60.

33. The process of claim 30, wherein p is 2.

34. The process of claim 26, wherein p is an integer in the range of about 10 to about 25.

35. The process of claim 34, wherein each Q is O, each r is 1, each R$_2$ is independently H, OH, protected OH, OCH$_3$ or OCH$_2$CH$_2$OCH$_3$.

36. A process of deprotecting a phosphorus-protected oligonucleotide, the process comprising contacting said phosphorus-protected oligonucleotide with a non-malodorous deprotecting agent for a time sufficient to remove the phosphorus protecting group, said phosphorus protecting group being alkyl, wherein said non-malodorous deprotecting agent is 2-methyl-5-t-butylthiophenol.

37. The process of claim 36, wherein the phosphorus protecting group is unsubstituted C$_1$–C$_{10}$ alkyl.

38. The process of claim 37, wherein the phosphorus protecting group is methyl.

39. The method of claim 2, wherein said monomeric nucleoside includes at least one of a ribonucleoside, a 2'-deoxynucleoside, a 2'-modified nucleoside, a locked nucleoside, a sugar-modified nucleoside, a base-modified nucleoside, an erythro-nucleoside, or an arabino-nucleoside.

40. The method of claim 3, wherein R$_5$ further comprises at least one of a halo, nitro, nitroso, OH, SH, CN, phenyl, phenoxy, benzyloxy, heteroaryl, partially saturated heterocyclyl, fully saturated heterocyclyl, or silyl group.

41. The method of claim 5, wherein said monomeric nucleoside includes at least one of a ribonucleoside, a 2'-deoxynucleoside, a 2'-modified nucleoside, a locked nucleoside, a sugar-modified nucleoside, a base-modified nucleoside, an erythro-nucleoside, or an arabino-nucleoside.

42. The method of claim 7, wherein said W and V monomeric nucleosides each optionally include at least one of a ribonucleoside, a 2'-deoxynucleoside, a 2'-modified nucleoside, a locked nucleoside, a sugar-modified nucleoside, a base-modified nucleoside, an erythro-nucleoside, or an arabino-nucleoside.

43. The method of claim 13, wherein said W and V monomeric nucleosides each optionally include at least one of a ribonucleoside, a 2'-deoxynucleoside, a 2'-modified nucleoside, a locked nucleoside, a sugar-modified nucleoside, a base-modified nucleoside, an erythro-nucleoside, or an arabino-nucleoside.

44. The method of claim 36, wherein the alkyl phosphorus protecting group further comprises at least one of a halo, nitro, nitroso, OH, SH, CN, phenyl, phenoxy, benzyloxy, heteroaryl, partially saturated heterocyclyl, fully saturated heterocyclyl, or silyl group.

* * * * *

UNITED STATES PATENT AND TRADEMARK OFFICE
CERTIFICATE OF CORRECTION

PATENT NO. : 6,967,247 B2
DATED : November 22, 2005
INVENTOR(S) : Vasulinga Ravikumar It is certified that error appears in the above-identified patent and that said Letters Patent is hereby corrected as shown below:

Column 39,
Line 43, delete "compounds" and insert -- compound --;

Column 42,
Line 4, insert -- protected OH, -- between "OH," and "SH";
Lines 40 and 41, insert -- , -- after "moiety";

Column 44,
Line 11, delete "in" and insert -- m --;
Line 13, delete "0" and insert -- O --;

Column 46,
Line 39, delete "20" and insert -- 30 --;
Line 42, delete "30" and insert -- 26 --.

Signed and Sealed this

Thirtieth Day of May, 2006

JON W. DUDAS
*Director of the United States Patent and Trademark Office*

SEQUENCE LISTING

<160> NUMBER OF SEQ ID NOS: 10

<210> SEQ ID NO 1
<211> LENGTH: 20
<212> TYPE: DNA
<213> ORGANISM: Artificial
<220> FEATURE:
<223> OTHER INFORMATION: Synthetic Construct

<400> SEQUENCE: 1
tcccgcctgt gacatgcatt                                                    20

<210> SEQ ID NO 2
<211> LENGTH: 20
<212> TYPE: DNA
<213> ORGANISM: Artificial
<220> FEATURE:
<223> OTHER INFORMATION: Synthetic Construct

<400> SEQUENCE: 2
gcccaagctg gcatccgtca                                                    20

<210> SEQ ID NO 3
<211> LENGTH: 21
<212> TYPE: DNA
<213> ORGANISM: Artificial
<220> FEATURE:
<223> OTHER INFORMATION: Synthetic Construct

<400> SEQUENCE: 3
gcgtttgctc ttcttcttgc g                                                  21

<210> SEQ ID NO 4
<211> LENGTH: 20
<212> TYPE: DNA
<213> ORGANISM: Artificial
<220> FEATURE:
<223> OTHER INFORMATION: Synthetic Construct

<400> SEQUENCE: 4
gttctcgctg gtgagtttca                                                    20

```
<210> SEQ ID NO 5
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate

<400> SEQUENCE: 5
tcccgcctgt gacatgcatt                                              20

<210> SEQ ID NO 6
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate

<400> SEQUENCE: 6
gcccaagctg gcatccgtca                                              20

<210> SEQ ID NO 7
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate
<220> FEATURE:
<221> NAME/KEY: misc_feature
<222> LOCATION: (13)..(20)
<223> OTHER INFORMATION: 2'-methoxyethyl

<400> SEQUENCE: 7
tcccgcctgt gacatgcatt                                              20

<210> SEQ ID NO 8
<211> LENGTH: 22
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 2'-methoxyethyl
<220> FEATURE:
<221> NAME/KEY: misc_feature
<222> LOCATION: (1)..(22)
<223> OTHER INFORMATION: phosphorothioate
<220> FEATURE:
<221> NAME/KEY: misc_feature
<222> LOCATION: (19)..(22)
<223> OTHER INFORMATION: 2'-methoxyethyl

<400> SEQUENCE: 8
cagcagcaga gtctttcatc at                                           22

<210> SEQ ID NO 9
<211> LENGTH: 20
<212> TYPE: DNA
```

```
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(6)
<223> OTHER INFORMATION: 2'-methoxyethyl
<220> FEATURE:
<221> NAME/KEY: misc_feature
<222> LOCATION: (1)..(20)
<223> OTHER INFORMATION: phosphorothioate
<220> FEATURE:
<221> NAME/KEY: misc_feature
<222> LOCATION: (15)..(20)
<223> OTHER INFORMATION: 2'-methoxyethyl

<400> SEQUENCE: 9
tcccgcctgt gacatgcatt                                               20

<210> SEQ ID NO 10
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(5)
<223> OTHER INFORMATION: 2'-methoxyethyl
<220> FEATURE:
<221> NAME/KEY: misc_feature
<222> LOCATION: (1)..(20)
<223> OTHER INFORMATION: phosphorothioate
<220> FEATURE:
<221> NAME/KEY: misc_feature
<222> LOCATION: (16)..(20)
<223> OTHER INFORMATION: 2'-methoxyethyl

<400> SEQUENCE: 10
gctgattaga gagaggtccc                                               20
```